United States Patent
Jongsma et al.

(10) Patent No.: US 6,861,578 B1
(45) Date of Patent: Mar. 1, 2005

(54) METHOD FOR PLANT PROTECTION AGAINST INSECTS OR NEMATODES BY TRANSFORMATION WITH A NUCLEIC ACID ENCODING EQUISTATIN

(75) Inventors: Maarten Anthonie Jongsma, Wageningen (NL); Borut Strukelj, Ljubljana (SI); Brigita Lenarcic, Ljubljana (SI); Kristina Gruden, Ljubliana (SI); Vito Turk, Ljubljana (SI); Hendrik J. Bosch, Utrecht (NL); Willem Johannes Stiekema, Wageningen (NL)

(73) Assignee: Plant Research International B.V., Wageningen (NL)

( * ) Notice: Subject to any disclaimer, the term of this patent is extended or adjusted under 35 U.S.C. 154(b) by 0 days.

(21) Appl. No.: 09/445,480

(22) PCT Filed: Jun. 18, 1998

(86) PCT No.: PCT/NL98/00352

§ 371 (c)(1),
(2), (4) Date: Jul. 7, 2000

(87) PCT Pub. No.: WO98/58068

PCT Pub. Date: Dec. 23, 1998

(30) Foreign Application Priority Data

Jun. 18, 1997 (EP) .............................. 97201777

(51) Int. Cl.[7] .............. A01H 5/00; C12N 15/82
(52) U.S. Cl. ................. 800/302; 800/279; 800/265; 435/320.1
(58) Field of Search ....................... 800/279, 288, 800/302, 265; 435/418, 419, 430, 320.1

(56) References Cited

FOREIGN PATENT DOCUMENTS

| EP | PCT/EP95/00881 | 3/1995 |
| WO | 92/21753 | * 12/1992 |

OTHER PUBLICATIONS

Lazar et al., Transforming Growth Factor x: Mutation of Aspartic Acid 47 and Leucine 48 Result in Different Biological Activities, Mar. 1988, Molecular and Cellular Biology, vol. 8, No. 3, pp. 1247–1252.*

Hill et al., Functional Analysis of Conserved Histidines in ADP–Glucose Pyrophosphorylase from *Eschetichia coli*, 1998, Biochemical and Biophysical Research Comm., vol. 244, pp. 573–577.*

Lenarcic, Brigita; Ritonja, Anka; Strukelj, Borut; Turk, Boris; and Turk, Vito. "Equistatin, a New Inhibitor of Cysteine Proteinases from Actinia equina, Is Structurally Related to Thyroglobulin Type–1 Domain." The Journal of Biological Chemistry, vol. 272, No. 21, pp. 13899–13903 and Addition or Correction Sheet (May 23, 1997).

Yamashita, Michiaki and Konagaya, Shiro. "A Novel Cysteine Protease Inhibitor of the Egg of Chum Salmon, Containing a Cysteinerich Thyroglobulin–like Motif." The Journal of Biological Chemistry, vol. 271, No. 3, pp. 1282–1284 (Jan. 19, 1996).

* cited by examiner

Primary Examiner—Anne Kubelik
(74) Attorney, Agent, or Firm—Thomas, Kayden, Horstemeyer, & Risley

(57) ABSTRACT

A method of protecting a plant or part of a plant from insect or nematode infestation is disclosed herein. The method includes the steps of: inserting into the genome of cells or tissue from a plant a sequence coding for equistatin operably linked to a promoter sequence active in the plant to cause expression of the protein at levels which provide an insect or nematode controlling amount of the protein; and regenerating resistant whole plants from the cells or tissue. Also disclosed is a transgenic plant or its sexual progeny which is resistant to attack by one or more insects or nematodes having digestive cysteine proteases. Also disclosed is an expression vehicle that includes a promotor effective to promote expression of a downstream coding sequence in plant cells, the expression vehicle being effective to express in plant cells insect controlling amounts of equistatin.

13 Claims, 13 Drawing Sheets

FIG. 1

```
  1    CTATGGCTCTTAGCCAAAACCAAGCCAAGTTTTCCAAAGGATTCGTCGTGATGATTTGG
 -32       M  A  L  S  Q  N  Q  A  K  F  S  K  G  F  V  V  M  I  W

60    GTACTATTCATTGCTTGTGCTATAACTTCAACTGAAGCTAGTCTAACCAAATGCCAACAG
-13     V  L  F  I  A  C  A  I  T  S  T  E  A  S  L  T  K  C  Q  Q
                                                        -1 +1
120    CTCCAGGCCTCGGCTAACAGTGGTCTGATAGGTACTTATGTACCACAATGCAAAGAAACG
  8     L  Q  A  S  A  N  S  G  L  I  G  T  Y  V  P  Q  C  K  E  T

180    GGAGAGTTCGAAGAAAAACAATGCTGGGGATCGACTGGTTACTGTTGGTGTGTGGATGAA
 28     G  E  F  E  E  K  Q  C  W  G  S  T  G  Y  C  W  C  V  D  E

240    GATGGAAAAGAGATTCTAGGAACCAAGATCCGTGGATCTCCGGATTGCAGCCGCAGAAAA
 48     D  G  K  E  I  L  G  T  K  I  R  G  S  P  D  C  S  R  R  K

300    GCCGCGTTAACACTTTGCCAGATGATGCAAGCCATCATTGTTAATGTCCCTGGTTGGTGT
 68     A  A  L  T  L  C  Q  M  M  Q  A  I  I  V  N  V  P  G  W  C

360    GGCCCTCCATCGTGTAAAGCTGACGGCAGTTTTGACGAGGTTCAGTGCTGCGCAAGTAAT
 88     G  P  P  S  C  K  A  D  G  S  F  D  E  V  Q  C  C  A  S  N

420    GGAGAATGCTACTGTGTGGATAAGAAAGGAAAAGAACTTGAAGGCACAAGACAACAGGGA
108     G  E  C  Y  C  V  D  K  K  G  K  E  L  E  G  T  R  Q  Q  G

480    AGGCCAACCTGCGAAAGACACCTAAGCGAATGCGAGGAAGCTCGAATCAAGGCGCATTCA
128     R  P  T  C  E  R  H  L  S  E  C  E  E  A  R  I  K  A  H  S

540    AACAGTCTTCGTGTTGAGATGTTCGTGCCAGAGTGTTTAGAAGATGGATCATATAACCCA
148     N  S  L  R  V  E  M  F  V  P  E  C  L  E  D  G  S  Y  N  P

600    GTACAGTGCTGGCCTAGCACAGGATACTGTTGGTGCGTCGATGAAGGAGGGGTAAAGGTA
168     V  Q  C  W  P  S  T  G  Y  C  W  C  V  D  E  G  G  V  K  V

660    CCAGGTTCCGATGTCAGATTTAAACGCCCCACATGCTAAGAAAAACACAGTGAACAAAGT
188     P  G  S  D  V  R  F  K  R  P  T  C  ---
                                         199
720    GGCTAGTTTCCAGATCGAAAATAACTACAAAGGATTAATAAAAATGTTAAAATAATTTCTC
780    AATTCGGCTGTGATATATTTTTTTCCAAGATAATTTAATCTGCATGTAGTTAACAGAAAAC
840    AATCTCAACTAGAAATAAAGACTACGGTAATAATGACAAAAAAAAAAAA
```

FIG. 2 thyroglobulin domains with demonstrated CPI activity

| | |
|---|---|
| human invariant chain | LITKCQ--BEVSHIPAVHPGSFRPKC-DENGNYLPLQCYGSIG--:--YCWCVFPNGTEVPNTRSR-GHHN-CSES |
| rat invariant chain (192-258) | KVLTKCQ--BEVSHIPDVHPGAFRPKV-DENGNYMPLQCHGSTG----YCWCVFPNGTEVPHTKSR-GRHN-CSEP |
| chum salmon egg inh. HVPIDGIFHLKTPCE--LARDAATHGPIGGFIPTC--DYNGQYTPEQCWGSTG----YCWCVNSSGQKLPGTDTPPGSASNC |
| equistatin cDNA DOMAIN I | SLTKCQ--QLQASANSGLIGTYVPQC--KETGEFEEKQCWGSTG----YCWCVDEDGKEILGTKIR-GSPD-CSRRK |
| equistatin purified domain I | SLSKCQ--QLQASANSGLIGAYVPQC--KETGEFEEKQCWGSTG----YCWCVDEDGKILGTKIR-GSPD-CSRRK |
| (protein sequence variants) | T V | thyroglobulin domains with demonstrated aspartic protease inhibitor activity (either domain II or III)

| | |
|---|---|
| equistatin cDNA DOMAIN II | AALTLCQ--MMQAIIVNVPGWCGPPSC-KADGSFDEVQCCASNG----ECYCVDKKGKELEGTRQQ-GRP-TCERHL |
| equistatin purified domain II | AALTLCQ--MMQAIIVNVPGWCGPPSC-KADGSFDEVQCCASNG----ECYCVDKKGKELEGTRQK-GRP-SCERHL |
| (protein sequence variants) | T |
| equistatin cDNA DOMAIN III | SECEEARIKAHSNSLRVEMFVPEC--LEDGSYNPVQCWPSTG----YCWCVDEGGVKVPGSDVRFKRP-TC |
| equistatin purified domain III | SPCEEARLQAHSNSLRVGMFVPQC--LEDGSYNPVQCWPSTG----YCWCVDEGGVKVPGSDVRPKRP-TC |
| (protein sequence variants) | E IK L D | thyroglobulin domains with unknown protease inhibitor activity

| | |
|---|---|
| mouse nidogen (824-892) | EHILGAAGGADAQRPTLQGMFVPQC--DEYGHYVPTQCHHSTG----YCWCVDRDGRELEGSRTPPGMRPPCLST |
| human epithelial glycoprot (75-146) | GSKLGRRAKPEGALQNNDGLYDPDC--DESGLFKAKQCNG-TS----MCWCVNTAGVRRTDKDYEIT----CSERVRTY |
| bull frog saxiphilin(178-226) | KCLKERQVALGGDEKVLGRFVPQC--DEKGNYEPQQFHGSTG----YSWCVNAIGEEIAGTKTPPGKIPAC |

```
Thyroglobulin 1.1 (29-73)                                                                YVPQC-AEDGSFQTVQCQNDGR-----SCHCVGANGSEVLGSRQP-GRPVAC
Thyroglobulin 1.2 (97-141)                                                               YLPQC-QDSGDYAPVQCDVQHV----QCWCVDAEGMEVYGTRQL-GRPKRC
Thyroglobulin 1.5 (597-639)                                                              FVPSC-TTEGSYEDVQCF-s-G----ECWCVNSWGKELPGSRVRDQP-RC
Thyroglobulin 1.6 (664-707)                                                              FVPAC-TSEGHFLPVQCFN--S----ECYCVDAEGQAIPGTRSAIGKPKKC
Bovine thyroglobulin (1143-1215)    QCPSLCEVLQSGVPSRRTSPGYSPACRAEDGGFSPVQCDPAQG-----SCHCVLGSQEEVPGTRVA-GSQPACESP
Mouse entactin (844-923)            KTRCQLEREHILGAAGGADAQRPTLQGMFVPQC-DEYGHYVPTQCHHSTG----YCWCVDRDGRELEGSRTPPGMRPPCLSTVAP
Human IGF-binding protein-3         YGPCRREMBDTLNHLKFLNVLSPRGVHIPNC-DKKGFYKKKQCRPSKQRKRGFCWCVDKYGQPLPGYTTKGKEDVHCYSMQSK
Human testican (305-381)            QKPGGLPCQNEMNRIGKLSKGKSLLGAFIPRC-NEEGYYKATQCHGSTG----QCWCVDKYGNELAGSRKQ-GAV-SCEEEQET consensus                           C--------//------------P-C-----G-----QC----------G------//-------CWCV---G-------C
```

FIG.2
(continue)

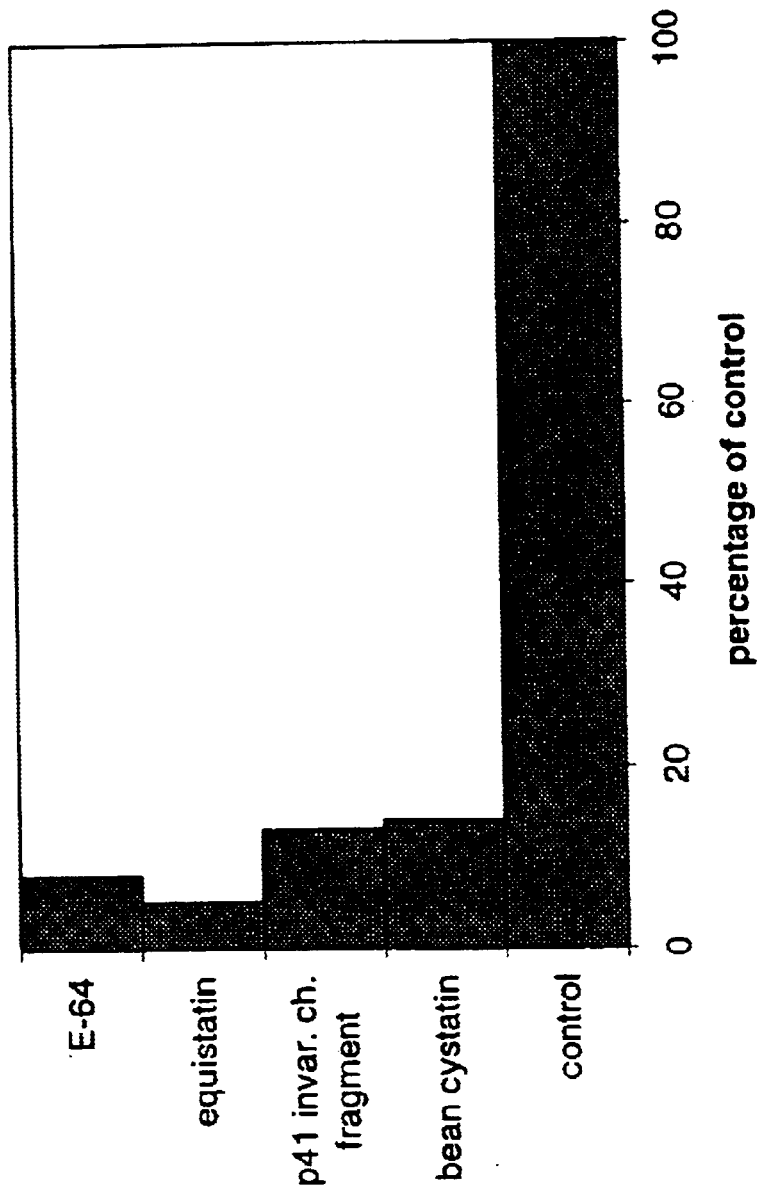

SEQUENCE LISTING

```
<160> NUMBER OF SEQ ID NOS: 31

<210> SEQ ID NO 1
<211> LENGTH: 888
<212> TYPE: DNA
<213> ORGANISM: Actinia equina
<300> PUBLICATION INFORMATION:
<301> AUTHORS: Gruden, Kristina; Strukelj, Borut; Popovic, Tatjana;
      Lenarcic, Brigita; Bevec, Tadeja; Brzin, Joze; Kregar, Igor;
      Herzog-Velikonja, Jana; Stiekema, Willem J; Bosch, Dirk
<302> TITLE: The Cysteine Protease Activity of Colorado Potato Beetle
      (Leptinotarsa decemlineata) Guts, Which is Insensitive to Potato
      Protease Inhibitors, is Inhibited by Thyroglobulin Type -1
<303> JOURNAL: Insect Biochem. Mol. Biol.
<304> VOLUME: 28
<306> PAGES: 549-560
<307> DATE: 1998

<400> SEQUENCE: 1
ctatggctct tagccaaaac caagccaagt tttccaaagg attcgtcgtg atgatttggg        60
tactattcat tgcttgtgct ataacttcaa ctgaagctag tctaaccaaa tgccaacagc       120
tccaggcctc ggctaacagt ggtctgatag gtacttatgt accacaatgc aaagaaacgg       180
gagagttcga agaaaaacaa tgctggggat cgactggtta ctgttggtgt gtggatgaag       240
atggaaaaga gattctagga accaagatcc gtggatctcc ggattgcagc cgcagaaaag       300
ccgcgttaac actttgccag atgatgcaag ccatcattgt taatgtccct ggttggtgtg       360
gccctccatc gtgtaaagct gacggcagtt ttgacgaggt tcagtgctgc gcaagtaatg       420
gagaatgcta ctgtgtggat aagaaaggaa aagaacttga aggcacaaga caacagggaa       480
ggccaacctg cgaaagacac ctaagcgaat gcgaggaagc tcgaatcaag gcgcattcaa       540
acagtcttcg tgttgagatg ttcgtgccag agtgtttaga agatggatca tataacccag       600
tacagtgctg gcctagcaca ggatactgtt ggtgcgtcga tgaaggaggg gtaaaggtac       660
caggttccga tgtcagattt aaacgcccca catgctaaga aaaacacagt gaacaaagtg       720
gctagtttcc agatcgaaaa taactacaaa ggattaataa aatgttaaaa taatttctca       780
attcggctgt gatatatttt ttccaagata atttaatctg catgtagtta acagaaaaca       840
atctcaacta gaaataaaga ctacggtaat aatgacaaaa aaaaaaaa                   888

<210> SEQ ID NO 2
```

<211> LENGTH: 231
<212> TYPE: PRT
<213> ORGANISM: Actinia equina

<400> SEQUENCE: 2

```
Met Ala Leu Ser Gly Ala Gly Ala Leu Pro Ser Leu Gly Pro Val Val
  1               5                  10                  15
Met Ile Thr Val Leu Pro Ile Ala Cys Ala Ile Thr Ser Thr Gly Ala
                 20                  25                  30
Ser Leu Thr Leu Cys Gly Gly Leu Gly Ala Ser Ala Ala Ser Gly Leu
             35                  40                  45
Ile Gly Thr Thr Val Pro Gly Cys Leu Gly Thr Gly Gly Pro Gly Gly
         50                  55                  60
Leu Gly Cys Thr Gly Ser Thr Gly Thr Cys Thr Cys Val Ala Gly Ala
 65                  70                  75                  80
Gly Leu Gly Ile Leu Gly Thr Leu Ile Ala Gly Ser Pro Ala Cys Ser
                 85                  90                  95
Ala Ala Leu Ala Ala Leu Thr Leu Cys Gly Met Met Gly Ala Ile Ile
                100                 105                 110
Val Ala Val Pro Gly Thr Cys Gly Pro Pro Ser Cys Leu Ala Ala Gly
            115                 120                 125
Ser Pro Ala Gly Val Gly Cys Cys Ala Ser Ala Gly Gly Cys Thr Cys
        130                 135                 140
Val Ala Leu Leu Gly Leu Gly Leu Gly Gly Thr Ala Gly Gly Gly Ala
145                 150                 155                 160
Pro Thr Cys Gly Ala His Leu Ser Gly Cys Gly Gly Ala Ala Ile Leu
                165                 170                 175
Ala His Ser Ala Ser Leu Ala Val Gly Met Pro Val Pro Gly Cys Leu
            180                 185                 190
Gly Ala Gly Ser Thr Ala Pro Val Gly Cys Thr Pro Ser Thr Gly Thr
        195                 200                 205
Cys Thr Cys Val Ala Gly Gly Val Leu Val Pro Gly Ser Ala Val
    210                 215                 220
Ala Pro Leu Ala Pro Thr Cys
225                 230
```

<210> SEQ ID NO 3
<211> LENGTH: 696
<212> TYPE: DNA
<213> ORGANISM: artificial sequence
<220> FEATURE:
<223> OTHER INFORMATION: synthetic sequence

<400> SEQUENCE: 3

```
atggctctta gccagaacca ggccaagttt tccaagggat tcgtcgtgat gatttgggta      60
ctattcattg cttgtgctat cacttcaact gaagctagtc taacgaaatg ccaacagctg     120
caggcctcgg ctaacagtgg tctgataggt acttatgtac acaatgcaa agaaactgga      180
gagtttgaag aaaagcaatg ctggggatcg actggttact gttggtgtgt ggatgaagat     240
ggaaaagaga ttctaggtac aaagatccgt ggatctccag actgcagtcg cagaaaagct     300
gccttaacac tttgccagat gatgcaagcc atcattgtga atgtccctgg ttggtgtgga     360
cctccatcat gtaaagctga cggcagtttt gacgaggttc agtgctgcgc aagtaatgga     420
gaatgctact gtgtggataa gaaggaaaa gaacttgaag gcacaagaca cagggaagg      480
ccaacctgcg aaagacacct aagcgaatgc gaggaggctc gtatcaaggc acattcaaac     540
```

```
agtcttcgtg ttgagatgtt cgtgccagag tgtttagaag atggatctta caaccctgta    600
cagtgctggc ctagcacagg atactgttgg tgcgtcgatg aaggagggt aaaggttcca     660 ggttccgacg tcagattcaa acgtcccaca tgctaa                              696
```

```
<210> SEQ ID NO 4
<211> LENGTH: 231
<212> TYPE: PRT
<213> ORGANISM: artificial sequence
<220> FEATURE:
<223> OTHER INFORMATION: synthetic sequence

<400> SEQUENCE: 4

Met Ala Leu Ser Gly Ala Gly Ala Leu Pro Ser Leu Gly Pro Val Val
1               5                   10                  15

Met Ile Thr Val Leu Pro Ile Ala Cys Ala Ile Thr Ser Thr Gly Ala
            20                  25                  30

Ser Leu Thr Leu Cys Gly Gly Leu Gly Ala Ser Ala Ala Ser Gly Leu
        35                  40                  45

Ile Gly Thr Thr Val Pro Gly Cys Leu Gly Thr Gly Gly Pro Gly Gly
    50                  55                  60

Leu Gly Cys Thr Gly Ser Thr Gly Thr Cys Thr Val Ala Gly Ala
65                  70                  75                  80

Gly Leu Gly Ile Leu Gly Thr Leu Ile Ala Gly Ser Pro Ala Cys Ser
                85                  90                  95

Ala Ala Leu Ala Ala Leu Thr Leu Cys Gly Met Met Gly Ala Ile Ile
            100                 105                 110

Val Ala Val Pro Gly Thr Cys Gly Pro Pro Ser Cys Leu Ala Ala Gly
        115                 120                 125

Ser Pro Ala Gly Val Gly Cys Cys Ala Ser Ala Gly Gly Cys Thr Cys
    130                 135                 140

Val Ala Leu Leu Gly Leu Gly Leu Gly Gly Thr Ala Gly Gly Gly Ala
145                 150                 155                 160

Pro Thr Cys Gly Ala His Leu Ser Gly Cys Gly Gly Ala Ala Ile Leu
                165                 170                 175

Ala His Ser Ala Ser Leu Ala Val Gly Met Pro Val Pro Gly Cys Leu
            180                 185                 190

Gly Ala Gly Ser Thr Ala Pro Val Gly Cys Thr Pro Ser Thr Gly Thr
        195                 200                 205

Cys Thr Cys Val Ala Gly Gly Gly Val Leu Val Pro Gly Ser Ala Val
    210                 215                 220

Ala Pro Leu Ala Pro Thr Cys
225                 230
```

```
<210> SEQ ID NO 5
<211> LENGTH: 18
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n = A, C, G, T
<220> FEATURE:
<221> NAME/KEY: misc_feature
<222> LOCATION: (6)..(6)
<223> OTHER INFORMATION: n = A, C, G, T
<220> FEATURE:
<221> NAME/KEY: misc_feature
<222> LOCATION: (9)..(9)
```

```
<223> OTHER INFORMATION: n = A, G
<220> FEATURE:
<221> NAME/KEY: misc_feature
<222> LOCATION: (12)..(12)
<223> OTHER INFORMATION: n = T, C
<220> FEATURE:
<221> NAME/KEY: misc_feature
<222> LOCATION: (15)..(15)
<223> OTHER INFORMATION: n = A, G
<220> FEATURE:
<221> NAME/KEY: misc_feature
<222> LOCATION: (18)..(18)
<223> OTHER INFORMATION: n = A, G

<400> SEQUENCE: 5
ctnacnaant gncancan                                                      18

<210> SEQ ID NO 6
<211> LENGTH: 21
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (4)..(4)
<223> OTHER INFORMATION: n = A, G
<220> FEATURE:
<221> NAME/KEY: misc_feature
<222> LOCATION: (7)..(7)
<223> OTHER INFORMATION: n = A, C, G, T
<220> FEATURE:
<221> NAME/KEY: misc_feature
<222> LOCATION: (10)..(10)
<223> OTHER INFORMATION: n = A, C, G, T
<220> FEATURE:
<221> NAME/KEY: misc_feature
<222> LOCATION: (13)..(13)
<223> OTHER INFORMATION: n = A, C, G, T
<220> FEATURE:
<221> NAME/KEY: misc_feature
<222> LOCATION: (16)..(16)
<223> OTHER INFORMATION: n = T, C
<220> FEATURE:
<221> NAME/KEY: misc_feature
<222> LOCATION: (19)..(49)
<223> OTHER INFORMATION: n = A, G

<400> SEQUENCE: 6
attnacntgn ggncgnttna a                                                  21

<210> SEQ ID NO 7
<211> LENGTH: 48
<212> TYPE: PRT
<213> ORGANISM: artificial sequence
<220> FEATURE:
<223> OTHER INFORMATION: conserved sequence
<220> FEATURE:
<221> NAME/KEY: MISC_FEATURE
<222> LOCATION: (1)..(48)
<223> OTHER INFORMATION: X = any amino acid

<400> SEQUENCE: 7

Cys Xaa Xaa Xaa Xaa Xaa Xaa Xaa Xaa Xaa Xaa Xaa Pro Xaa Cys
1               5                   10                  15

Xaa Xaa Xaa Gly Xaa Xaa Xaa Xaa Xaa Gly Cys Xaa Xaa Xaa Xaa
            20                  25                  30

Xaa Cys Thr Cys Val Xaa Xaa Xaa Gly Xaa Xaa Xaa Xaa Xaa Cys
        35                  40                  45

<210> SEQ ID NO 8
```

```
<211> LENGTH: 7
<212> TYPE: PRT
<213> ORGANISM: artificial sequence
<220> FEATURE:
<223> OTHER INFORMATION: synthetic substrate
<220> FEATURE:
<221> NAME/KEY: misc_feature
<222> LOCATION: (5)..(5)
<223> OTHER INFORMATION: x=nitrophenylalanine

<400> SEQUENCE: 8

Pro Thr Gly Pro Xaa Ala Leu
1               5

<210> SEQ ID NO 9
<211> LENGTH: 30
<212> TYPE: DNA
<213> ORGANISM: artificial sequence
<220> FEATURE:
<223> OTHER INFORMATION: primer

<400> SEQUENCE: 9
cgcgccatgg cgagtctaac caaatgccaa                              30

<210> SEQ ID NO 10
<211> LENGTH: 30
<212> TYPE: DNA
<213> ORGANISM: artificial sequence
<220> FEATURE:
<223> OTHER INFORMATION: primer

<400> SEQUENCE: 10
gggtgcggcc gcgcatgtgg ggcgtttaaa                              30

<210> SEQ ID NO 11
<211> LENGTH: 31
<212> TYPE: DNA
<213> ORGANISM: artificial sequence
<220> FEATURE:
<223> OTHER INFORMATION: primer

<400> SEQUENCE: 11 ggggggaat tcctgacctc ttactaactc g                             31

<210> SEQ ID NO 12
<211> LENGTH: 47
<212> TYPE: DNA
<213> ORGANISM: artificial sequence
<220> FEATURE:
<223> OTHER INFORMATION: primer

<400> SEQUENCE: 12
gggggggagc tcagatcttg ccatggtttt tcttctcttt tttttg            47

<210> SEQ ID NO 13
<211> LENGTH: 30
<212> TYPE: DNA
<213> ORGANISM: artificial sequence
<220> FEATURE:
<223> OTHER INFORMATION: primer

<400> SEQUENCE: 13
agatctgagc tctcgttcaa acatttggca                              30

<210> SEQ ID NO 14
<211> LENGTH: 27
<212> TYPE: DNA
```

```
<213> ORGANISM: artificial sequence
<220> FEATURE:
<223> OTHER INFORMATION: primer

<400> SEQUENCE: 14
aagcttgaat tcgatctagt aacatag                                              27

<210> SEQ ID NO 15
<211> LENGTH: 24
<212> TYPE: DNA
<213> ORGANISM: artificial sequence
<220> FEATURE:
<223> OTHER INFORMATION: primer

<400> SEQUENCE: 15
ggggccatgg ctcttagcca aaac                                                 24

<210> SEQ ID NO 16
<211> LENGTH: 32
<212> TYPE: DNA
<213> ORGANISM: artificial sequence
<220> FEATURE:
<223> OTHER INFORMATION: primer

<400> SEQUENCE: 16
gggggagatc tttagcatgt ggggcgttta aa                                        32

<210> SEQ ID NO 17
<211> LENGTH: 6
<212> TYPE: PRT
<213> ORGANISM: artificial sequence
<220> FEATURE:
<223> OTHER INFORMATION: conserved sequence

<400> SEQUENCE: 17

Gly Thr Cys Thr Cys Val
1               5

<210> SEQ ID NO 18
<211> LENGTH: 65
<212> TYPE: PRT
<213> ORGANISM: Human Invariant Chain

<400> SEQUENCE: 18

Leu Thr Lys Cys Gln Glu Val Ser His Ile Pro Ala Val His Pro
1               5                   10                  15

Gly Ser Phe Arg Pro Lys Cys Asp Glu Asn Gly Asn Tyr Leu Pro Leu
            20                  25                  30

Gln Cys Tyr Gly Ser Ile Gly Tyr Cys Trp Cys Val Phe Pro Asn Gly
        35                  40                  45

Thr Glu Val Pro Asn Thr Arg Ser Arg Gly His His Asn Cys Ser Glu
    50                  55                  60

Ser
65

<210> SEQ ID NO 19
<211> LENGTH: 67
<212> TYPE: PRT
<213> ORGANISM: rat invariant chain

<400> SEQUENCE: 19

Lys Val Leu Thr Lys Cys Gln Glu Glu Val Ser His Ile Pro Asp Val
1               5                   10                  15
```

```
His Pro Gly Ala Phe Arg Pro Lys Val Asp Glu Asn Gly Asn Tyr Met
            20                  25                  30

Pro Leu Gln Cys His Gly Ser Thr Gly Tyr Cys Trp Cys Val Phe Pro
            35                  40                  45

Asn Gly Thr Glu Val Pro His Thr Lys Ser Arg Gly Arg His Asn Cys
        50                  55                  60

Ser Glu Pro
65

<210> SEQ ID NO 20
<211> LENGTH: 74
<212> TYPE: PRT
<213> ORGANISM: chum salmon egg inh.

<400> SEQUENCE: 20

His Val Pro Ile Asp Gly Ile Phe His Leu Lys Thr Pro Cys Glu Leu
1               5                   10                  15

Ala Arg Asp Ala Ala Thr His Gly Pro Ile Gly Phe Ile Pro Thr
            20                  25                  30

Cys Asp Tyr Asn Gly Gln Tyr Thr Pro Glu Gln Cys Trp Gly Ser Thr
            35                  40                  45

Gly Tyr Cys Trp Cys Val Asn Ser Ser Gly Gln Lys Leu Pro Gly Thr
        50                  55                  60

Asp Thr Pro Pro Gly Ser Ala Ser Asn Cys
65                  70

<210> SEQ ID NO 21
<211> LENGTH: 69
<212> TYPE: PRT
<213> ORGANISM: Mouse Nidogen

<400> SEQUENCE: 21

Glu His Ile Leu Gly Ala Ala Gly Gly Ala Asp Ala Gln Arg Pro Thr
1               5                   10                  15

Leu Gln Gly Met Phe Val Pro Gln Cys Asp Glu Tyr Gly His Tyr Val
            20                  25                  30

Pro Thr Gln Cys His His Ser Thr Gly Tyr Cys Trp Cys Val Asp Arg
            35                  40                  45

Asp Gly Arg Glu Leu Glu Gly Ser Arg Thr Pro Pro Gly Met Arg Pro
        50                  55                  60

Pro Cys Leu Ser Thr
65

<210> SEQ ID NO 22
<211> LENGTH: 68
<212> TYPE: PRT
<213> ORGANISM: Human Epithelial Glycoprot

<400> SEQUENCE: 22

Gly Ser Lys Leu Gly Arg Arg Ala Lys Pro Glu Gly Ala Leu Gln Asn
1               5                   10                  15

Asn Asp Gly Leu Tyr Asp Pro Asp Cys Asp Glu Ser Gly Leu Phe Lys
            20                  25                  30

Ala Lys Gln Cys Asn Gly Thr Ser Met Cys Trp Cys Val Asn Thr Ala
            35                  40                  45

Gly Val Arg Arg Thr Asp Lys Asp Thr Glu Ile Thr Cys Ser Glu Arg
        50                  55                  60

Val Arg Thr Tyr
```

-continued

<210> SEQ ID NO 23
<211> LENGTH: 65
<212> TYPE: PRT
<213> ORGANISM: Bull Frog Saxiphilin

<400> SEQUENCE: 23

Lys Cys Leu Lys Glu Arg Gln Val Ala Leu Gly Gly Asp Glu Lys Val
1               5                   10                  15

Leu Gly Arg Phe Val Pro Gln Cys Asp Glu Lys Gly Asn Tyr Glu Pro
            20                  25                  30

Gln Gln Phe His Gly Ser Thr Gly Tyr Ser Trp Cys Val Asn Ala Ile
        35                  40                  45

Gly Glu Glu Ile Ala Gly Thr Lys Thr Pro Pro Gly Lys Ile Pro Ala
    50                  55                  60

Cys
65

<210> SEQ ID NO 24
<211> LENGTH: 45
<212> TYPE: PRT
<213> ORGANISM: Thyroglobulin 1.1

<400> SEQUENCE: 24

Tyr Val Pro Gln Cys Ala Glu Asp Gly Ser Phe Gln Thr Val Gln Cys
1               5                   10                  15

Gln Asn Asp Gly Arg Ser Cys Trp Cys Val Gly Ala Asn Gly Ser Glu
            20                  25                  30

Val Leu Gly Ser Arg Gln Pro Gly Arg Pro Val Ala Cys
        35                  40                  45

<210> SEQ ID NO 25
<211> LENGTH: 45
<212> TYPE: PRT
<213> ORGANISM: Thyroglobulin 1.2

<400> SEQUENCE: 25

Tyr Leu Pro Gln Cys Gln Asp Ser Gly Asp Tyr Ala Pro Val Gln Cys
1               5                   10                  15

Asp Val Gln His Val Gln Cys Trp Cys Val Asp Ala Glu Gly Met Glu
            20                  25                  30

Val Tyr Gly Thr Arg Gln Leu Gly Arg Pro Lys Arg Cys
        35                  40                  45

<210> SEQ ID NO 26
<211> LENGTH: 43
<212> TYPE: PRT
<213> ORGANISM: Thyroglobulin 1.5

<400> SEQUENCE: 26

Phe Val Pro Ser Cys Thr Thr Glu Gly Ser Tyr Glu Asp Val Gln Cys
1               5                   10                  15

Phe Ser Gly Glu Cys Trp Cys Val Asn Ser Trp Gly Lys Glu Leu Pro
            20                  25                  30

Gly Ser Arg Val Arg Asp Gly Gln Pro Arg Cys
        35                  40

<210> SEQ ID NO 27
<211> LENGTH: 44

```
<212> TYPE: PRT
<213> ORGANISM: Thyroglobulin 1.6

<400> SEQUENCE: 27

Phe Val Pro Ala Cys Thr Ser Glu Gly His Phe Leu Pro Val Gln Cys
1               5                   10                  15

Phe Asn Ser Glu Cys Tyr Cys Val Asp Ala Glu Gly Gln Ala Ile Pro
            20                  25                  30

Gly Thr Arg Ser Ala Ile Gly Lys Pro Lys Lys Cys
        35                  40

<210> SEQ ID NO 28
<211> LENGTH: 70
<212> TYPE: PRT
<213> ORGANISM: Bovine Thyroglobulin

<400> SEQUENCE: 28

Gln Cys Pro Ser Leu Cys Glu Val Leu Gln Ser Gly Val Pro Ser Arg
1               5                   10                  15

Arg Thr Ser Pro Gly Tyr Ser Pro Ala Cys Arg Ala Glu Asp Gly Gly
            20                  25                  30

Phe Ser Pro Val Gln Cys Asp Pro Ala Gln Gly Ser Cys Trp Cys Val
        35                  40                  45

Leu Gly Ser Gly Glu Glu Val Pro Gly Thr Arg Val Ala Gly Ser Gln
    50                  55                  60

Pro Ala Cys Glu Ser Pro
65                  70

<210> SEQ ID NO 29
<211> LENGTH: 80
<212> TYPE: PRT
<213> ORGANISM: Mouse Entactin

<400> SEQUENCE: 29

Lys Thr Arg Cys Gln Leu Glu Arg Glu His Ile Leu Gly Ala Ala Gly
1               5                   10                  15

Gly Ala Asp Ala Gln Arg Pro Thr Leu Gln Gly Met Phe Val Pro Gln
            20                  25                  30

Cys Asp Glu Tyr Gly His Tyr Val Pro Thr Gln Cys His His Ser Thr
        35                  40                  45

Gly Tyr Cys Trp Cys Val Asp Arg Asp Gly Arg Glu Leu Glu Gly Ser
    50                  55                  60

Arg Thr Pro Pro Gly Met Arg Pro Pro Cys Leu Ser Thr Val Ala Pro
65                  70                  75                  80

<210> SEQ ID NO 30
<211> LENGTH: 82
<212> TYPE: PRT
<213> ORGANISM: Human IGF-Binding Protein-3

<400> SEQUENCE: 30

Tyr Gly Pro Cys Arg Arg Glu Met Glu Asp Thr Leu Asn His Leu Lys
1               5                   10                  15

Phe Leu Asn Val Leu Ser Pro Arg Gly Val His Ile Pro Asn Cys Asp
            20                  25                  30

Lys Lys Gly Phe Tyr Lys Lys Gln Cys Arg Pro Ser Lys Gly Arg
        35                  40                  45

Lys Arg Gly Phe Cys Trp Cys Val Asp Lys Tyr Gly Gln Pro Leu Pro
    50                  55                  60
```

```
Gly Tyr Thr Thr Lys Gly Lys Glu Asp Val His Cys Tyr Ser Met Gln
65                  70                  75                  80

Ser Lys

<210> SEQ ID NO 31
<211> LENGTH: 77
<212> TYPE: PRT
<213> ORGANISM: Human Testican

<400> SEQUENCE: 31

Gln Lys Pro Gly Gly Leu Pro Cys Gln Asn Glu Met Asn Arg Ile Gly
1               5                   10                  15

Lys Leu Ser Lys Gly Lys Ser Leu Leu Gly Ala Phe Ile Pro Arg Cys
                20                  25                  30

Asn Glu Glu Gly Tyr Tyr Lys Ala Thr Gln Cys His Gly Ser Thr Gly
            35                  40                  45

Gln Cys Trp Cys Val Asp Lys Tyr Gly Asn Glu Leu Ala Gly Ser Arg
        50                  55                  60

Lys Gln Gly Ala Val Ser Cys Glu Glu Glu Gln Glu Thr
65                  70                  75
```

METHOD FOR PLANT PROTECTION AGAINST INSECTS OR NEMATODES BY TRANSFORMATION WITH A NUCLEIC ACID ENCODING EQUISTATIN

CROSS-REFERENCE TO RELATED APPLICATIONS

This application claims priority to International patent application no. PCT/NL98/00352, filed Jun. 18, 1998.

This invention relates to a method of protecting a plant or a part of said plant against insect or nematode infestation by one or more insects or nematodes having digestive cysteine and/or aspartic proteases, comprising presenting to a locus wherein said insect (s) or nematode(s) is to be controlled an inhibitory amount of a cysteine and/or aspartic protease inhibitor.

Many vegetables, horticultural and field crops are attacked by insect pests. Most plants show some resistance to certain insects or nematodes; the resistance can be physical or chemical. For example, the hairs on the leaves of many plants can stop small insects from getting near enough to the surface to chew it. In other cases plants use a range of complex molecules to make their tissues unattractive or toxic. Control of such phytophagous insects and nematodes has traditionally been partially addressed by cultural and breeding methods. An effective way to reduce these losses is to use crop cultivars having genes for pest resistance (see Painter (1951), Insect Resistance in Crop Plants, Macmillan: New York). Plant breeders have attempted to reduce losses caused by insect and nematode attack by incorporating resistance genes into their varieties via conventional breeding programs.

Classical approaches to host plant resistance, though remarkably successful in some instances, are rather empirical. Once "traits" for resistance are discovered they are moved into agronomically acceptable lines by selection procedures. One limitation of the classical approach is that the movement of genes for resistance from one plant to another is restricted to species that can be interbred.

Additionally, these types of resistance may be under the control of many genes, and so are difficult for the plant breeder to exploit. Often resistant varieties have shown a yield depression and so have not been economically viable. Moreover, if no resistance can be identified within a species or within related species then no improvement in insect pest resistance is possible by classical breeding.

Chemical pesticides have been heavily relied upon to control insects and nematodes. These agents typically are applied on or banded into the soil, or to plant foliage or in bait stations. In spite of the availability of a wide range of chemical pesticides, phytophagous insects and plant parasitic nematodes remain a serious problem. Many chemical pesticides have the disadvantage of requiring repeated applications. A major problem in the use of many pesticides is the ability of insects to become resistant to the applied agents. This phenomenon occurs through selection of the most resistant members of the insect population during repeated application of the agent. In addition, these chemicals are environmentally damaging and polluting the water table. A need, therefore, exists for new insect control agents, particularly agents that have a mode of action different from conventional insecticides and nematicides.

As alternatives to synthetic compounds, certain naturally-occurring agents have been isolated and developed as pesticides. These include plant and microbial secondary metabolites and proteins, and natural predators or pathogens of insects or nematodes (including other insects, fungi, bacteria, and viruses). Furthermore as recombinant DNA technology has advanced, genes from a donor organism may be transferred to a recipient organism resulting in a new phenotype in the recipient. In the case of transgenic plants, this phenotype may be resistance to insect damage or nematode infection if the introduced gene encodes a polypeptide, the action of which results in a deleterious effect on the pest. Consequently, there is a great interest and utility in finding polypeptides that have such an effect. Genes for these polypeptides can be used to modify organisms, especially plants and microbes, so that they adversely affect the growth and development of insect pests. A number of such polypeptides have been described from *Bacillus thuringiensis*, various proteinaceous protease and amylase inhibitors, and various plant lectins.

One physiological system of insects and nematodes known to be susceptible to disruption by specific inhibitors is the action of digestive proteases. The digestive proteases hydrolyze ingested proteins and polypeptides by cleaving peptide bonds. The term "protease" is specifically intended to include endopeptidases and exopeptidases of the four major catalytic classes: serine proteases, cysteine proteases, aspartic proteases and metallo proteases (see Laskowski et al. (1983), *Ann. Rev. Biochem.*, 49: 593–626). The class to which a specific protease belongs can be determined by the pH range over which it is active, by its ability to hydrolyze specific proteins, by its similarity to other well-characterized proteases and by its sensitivity to various inhibitors.

Diverse types of insect and nematode digestive enzymes release peptides and amino acids from dietary protein. One class of digestive enzymes is the class of cysteine proteases. The term "cysteine protease" is intended to describe a protease that possesses a highly reactive thiol group of a cysteine residue at the catalytic site of the enzyme. There is evidence that many phytophagous insects and plant parasitic nematodes rely, at least in part, on midgut cysteine proteases for protein digestion. These include but are not limited to Hemiptera, especially squash bugs (*Anasa tristis*); green stink bug (*Acrosternum hilare*); *Riptortus clavatus*; and almost all Coleootera examined so far, especially, Colorado potato beetle (*Leptinotarsa deoemlineata*); three-lined potato beetle (*Lema trilineata*); asparagus beetle (*Crioceris asparagi*); Mexican bean beetle (*Epilachna varivestis*); red flour beetle (*Tribolium castaneum*); confused flour beetle (*Tribolium corfusum*); the flea beetles (*Chaetocnema* spp., *Haltica* spp. and *Epitrix* spp.); corn rootworm (*Diabrotica* Spp.); cowpea weevil (*Callosobruchus maculatus*); boll weevil (*Anthonomus grandis*); rice weevil (*Sitophilus oryza*); maize weevil (*Sitophilus zeamais*); granary weevil (*Sitophilus granarius*); Egyptian alfalfa weevil (*Hypera postica*); bean weevil (*Acanthoscelides obtectus*); lesser grain borer (*Rhyzopertha dominica*); yellow meal worm (*Tenebrio molitor*); Thysanoptera, especially, western flower thrips (*Frankliniella occidentalis*); Diptera, especially, leafminer spp. (*Liriomyza trifolii*); plant parasitic nematodes especially the potato cyst nematodes (*Globodera* spp.), the beet cyst nematode (*Heterodera schachtii*) and root knot nematodes (*Meloidogyne* spp.).

Another class of digestive enzymes are the aspartic proteases. The term "aspartic protease" is intended to describe a protease that possesses two highly reactive aspartic acid residues at the catalytic site of the enzyme and which is most often characterized by its specific inhibition with pepstatin, a low molecular weight inhibitor of nearly all known aspartic proteases. There is evidence that many phytophagous insects rely, in part, on midgut aspartic proteases for protein digestion most often in conjunction with cysteine proteases. These include but are not limited to *Hemiptera* especially (*Rhodnius prolixus*) and bedbug (*Cimex* spp.) and members of the families Phymatidae, Pentatomidae, Lygaeidae and Belostomatidae; *Coleoptera*, in the families of the Meloidae, Chrysomelidae, Coccinelidae and Bruchidae all belonging to the series Cucujiformia, especially, Colorado potato beetle (*Leptinotarsa decemlineata*) three-lined potato beetle (*Lema trilineata*); southern and western corn rootworm (*Diabrotica undecimpunctata* and *D. virgifera*), boll weevil (*Anthonomus grandis*), squash bug (*Anasa tristis*); flea beetle (*Phyllotreta crucifera*), bruchid beetle (*Callosobruchus maculatus*), mexican bean beetle (*Epilachna varivestis*), soybean leafminer (*Odontota horni*) margined blister beetle (*Epicauta pestifera*) and the red flour beetle (*Tribolium castaneum*); *Diptera*, especially housefly (*Musca domestica*) (Terra and Ferreira (1994) *Coma. Biochem. Physiol.* 109B: 1–62; Wolfson and Murdock (1990) *J. Chem. Ecol.* 16: 1089–1102).

Compounds that form complexes with proteases and inhibit their proteolytic activity are widespread in nature. A variety of "low molecular weight" protease inhibitors are known, largely of non-natural synthetic origin. A number of naturally occurring low molecular weight inhibitors have been isolated from bacterial and fungal sources and characterized; this group includes such inhibitors as E64 (N-(L-3-trans carboxyoxiran-22-carbomyl)-L-leucyl-amido-4-guanidobutane), leupeptins, antipains and pepstatins.

Several proteinaceous protease inhibitors have been isolated from plant species and are among the defensive chemicals in plant tissues that are both developmentally regulated and induced in response to insect and pathogen attacks. Inhibitors of serine-, cysteine-, aspartic-, and metallo-proteases have been found in plants and especially in storage organs such as tubers and seeds. The most common and widely studied group of plant protease inhibitors are those that inhibit the animal serine proteases, which include trypsin and chymotrypsin (see Ryan (1990) *Annu. Rev. Phytopathol.* 28: 425–449).

Proteinaceous cysteine protease inhibitors decrease or eliminate the catalytic activity of a cysteine protease. The pH optima of cysteine proteases is usually in the range of 3.5–7, which is the pH range in the lumen of midguts of insects that use cysteine proteases. Inhibitors of cysteine proteases are dominated by the cystatin family which is subdivided into four subfamilies with respect to molecular weight, the number of disulphide bonds, subcellular localization, and primary structure characteristics. The classification system is mainly based on information regarding vertebrate and plant cystatins. Cystatins have been tested against insects and nematodes both in vitro and in vivo.

Very few other examples of proteinaceous inhibitors of cysteine proteases exist to date. From potato one other family of cysteine protease inhibitors is known which belongs to the plant Kunitz family of inhibitors and which also includes aspartic protease inhibitors (Strukelj (1992) *Biol. Chem. Hoppe-Seyler* 373: 477–482; Krizaj et al. (1993) *FEBS Letters* 333: 15–20). This inhibitor, Kunitz PCPI8.3, is a tight inhibitor of Cathepsin L (Ki=0.07 nM) and a good inhibitor of papain (Ki=3.3 nM). From *Diabrotica virgifera* a completely novel type of thiol protease inhibitor was isolated (World Patent Wo 95/24479). This inhibitor bears no structural relationship to other known cysteine protease inhibitors.

Recently, a new class of cysteine protease inhibitors emerged. These proteins have a type I repeated thyroglobulin domain in common (Malthiery and Lissitzky (1987) *Eur. J. Biochem.* 165: 491–498). From humans a protein fragment derived from human MHC class II-associated p41 invariant chain was isolated (Ogrinc et al. (1993) *FEBS Letters* 336: 555–559; Bevec et al. (1996) *J. Exp. Med.* 183: 1331–1338). It is a tight inhibitor of Cathepsin L (Ki=0.0017 nM) and a good inhibitor of papain (Ki=1.4 nM). A similar cysteine protease inhibitor with a type I repeated thyroglobulin domain was isolated from the eggs of chum salmon (Yamashita and Konagaya (1996) *J. Biol. Chem.* 271: 1282–1284). Finally, from the sea anemone, *Actinia equina*, a cysteine protease inhibitor designated equistatin was isolated with three type I repeated thyroglobulin domains (Lenarcic et al.(1997) *J. Biol. Chem.* 272: 13899; Lenarcic et al. (1998) *J. Biol. Chem.* 273: 12682).

Apart from human invariant chain, ECI (egg cysteine protease inhibitor) and equistatin, parts of other proteins also have domains homologous to type I repeated thyroglobulin domains, including proteins such as rat invariant chain (McKnight et al. (1989) *Nucleic Acids Res.* 17: 3983–3984), saxiphilin (Morabito and Moczydlowski (1994) *Proc. Natl. Acad. Sci. USA* 91: 2478–2482), nidogen (Mann et al. (1989) *EMBO J.* 8: 65–72), epithelial glycoprotein (Simon et al. (1990) *Proc. Natl. Acad. Sci. USA* 87: 2755–2759), IGF-binding protein-3 (Brewer et al. (1988) *Biochem. Biophys. Res. Commun.* 152: 1287–1289), testican (Alliel et al. (1993) *Eur. J. Biochem.* 214: 347–350) and entactin (Durkin et al. (1988) *J. Cell. Biol.* 107: 2749–2756) (FIG. 3). For entactin and thyroglobulin, it was published that they do not inhibit cysteine proteases (Yamashita and Konagaya (1996) *J. Biol. Chem.* 271: 1282–1284). These proteins do contain the conserved sequences and the reason for the lack of inhibition is obscure.

Proteinaceous aspartic protease inhibitors decrease or eliminate the catalytic activity of an aspartic protease. The pH optima of aspartic proteases is usually in the range of 2–5, which is the pH range in the parts of the gut where aspartic proteases are active. Very few proteinaceous inhibitors of aspartic proteases are known. One well characterized family of cathepsin D inhibitors is found in potato and related Solanaceae (Strukelj et al. (1992) *Biol. Chem. Hoppe-Seyler* 373:477–482). No in vitro enzymatic assay tests or in vivo bioassays have been published on the use of potato aspartic protease inhibitors against insects or nematodes.

Australian Patent Application No. 36558/89 teaches that animal cystatins (such as hen egg white cystatin and kininogens) and low molecular weight, non-peptide oysteine protease inhibitors (such as E-64, antipain and leupeptin) may be effective in the control of a variety of *Coleoptera* which utilize cysteine proteases for digestion.

WO 92/21753 teaches that multicystatin, an 8-domain phytocystatin from potato, is more effective than other cystatins in the control of a variety of insects utilizing cysteine proteases for digestion of protein in the midgut, because it is more resistant to proteolysis by carboxypeptidases.

WO 96/16173 teaches that modified cystatins can protect plants against nematodes.

WO 95/24479 teaches that a novel thio]protease inhibitor isolated from the corn rootworm and designated virgiferin can protect plants against insects and nematodes that have thiol proteases as digestive enzymes.

Evidence for these claims was published also in the scientific literature for different coleopteran and hemipteran insects as well as for nematodes (Chen et al. (1992) *Protein*

Express Purification 3: 41–49; Edmonds et al. (1996) Entomol. Exp. Appl. 78: 83–94; Elden (1995) J. Econ. Entomol. 88: 1586–1590; Orr et al. (1994) J. Insect Physiol. 40: 893–900; Kuroda et al. (1996) Biosci. Biotech. Biochem. 60: 209–212; Leplé et al. (1995) Molecular Breeding 1: 319–328; Urwin et al. (1995) Plant J. 8, 121–131). At high concentrations the cystatins caused mortality or reduced the fertility and growth of some insects and nematodes (Table 1). However, the cysteine protease inhibitor concentrations required to achieve agronomically interesting levels of protection in artificial diets (200–2000 $\mu$M, see Table 1) in most cases are much higher than can be achieved in transgenic plants (10–40 $\mu$M, see Table 1) and also much higher than the actual protease concentrations which they are expected to inhibit (10–30 $\mu$M). The high concentrations are required most likely because they do not bind all the different molecular forms of cysteine proteases present in the gut tightly enough weak inhibitors can still inhibit proteases when they are present in large excess to the protease. It is estimated that between 10 and 30 different proteolytic enzymes are active in the gut and the transcription of proteases that are not inhibited can be actively induced by the insect to compensate for the inhibition of other proteases (Jongsma et al. (1995) Proc. Natl. Acad. Sci USA 92: 8041–8045; Bolter and Jongsma (1995) J. Insect Physiol. 41: 1071–1078). A second reason for their lack of toxicity may be that they are unstable in the gut environment and degraded by proteases which are not inhibited.

The mere fact a protease inhibitor is an inhibitor of cysteine or aspartic proteases, therefore, does not necessarily mean it will be effective in vitro against insects utilizing these proteases for digestion (see also WO 92/21753). In general, it can be said that it is rare that any single inhibitor will completely inhibit the entire spectrum of cysteine or aspartic protease activity in an insect or nematode gut at a normal concentration that can be achieved in plants (10–40 $\mu$M). Inhibitors which at the same time inhibit both cysteine and aspartic proteases of a certain insect have never been described before, even though their utility is obvious, as many insects rely on the combination of these two classes of proteolytic enzymes for digestion. Many of the listed insects in table 1 rely on both types of proteases and the fact that the inhibitors are often not highly toxic to the insects is likely to be caused by the fact that the aspartic proteases remain free to digest the dietary protein and the cysteine protease inhibitors.

TABLE 1

Cysteine protease inhibitors that affect fitness parameters of insects when administered in diets or expressed in transgenic host plants

| Insect species | PI-level in diet/plant ($\mu$M) | Effect | Reference |
|---|---|---|---|
| Artificial diets supplemented with cystatins ||||
| Tribolium castaneum (Col.) | 10,000 | 35% WR | Chen et al., 1992 |
| Hepera postica (Col.) | 200 | RF | Elden 1995 |
| Diabrotica undecimpunctata (Col.) | 100–200 | 40–70% M | Edmonds et al., 1996 |
| Diabrotica undecimpunctata (Col.) | 125 $\mu$g/cm2 | 50% WR | Orr et al., 1994 |
| Diabrotica virgifera (Col.) | 125 $\mu$g/cm2 | 50% WR | Orr et al., 1994 |
| Callosobruchus chinensis (Col.) | 100–2,000 | 10–100% M | Kuroda et al., 1994 |
| Ripcortus clavatus (Hem.) | 100–2,000 | 0–100% M | Kuroda et al., 1996 |
| Transgenic plants expressing cystatins ||||
| Giobodera pallida (Nemat.) | 10 (tomato) | empty cyst | Urwin et al., 1995 |
| Chrysomela tremulae (Col.) | 40 (poplar) | 40% M | Leple et al., 1995 |

WR = weight reduction; RF = reduced fertility; M = mortality

Prior literature exists which demonstrates that some insects like the Colorado potato beetle are particularly insensitive to protease inhibitors, even when they are isolated from completely unrelated sources like rice or humans (Michaud et al. (1995) Insect Biochem. Molec. Biol. 25: 1041–1048; Michaud et al. (1996) Archives of Insects Biochemistry and Physiology 31: 451–464; Michaud et al. (1993) FEBS Letters 331: 173–176). Some of these protease inhibitors when tested against other insects were found to be quite effective (Leple et al. (1995) Molecular Breeding 1: 319–328). In Colorado potato beetle, however, these inhibitors were demonstrated to be either too specific for only one type of protease activity or to be broken down by aspartic proteases.

The structural requirements for a cysteine or aspartic protease inhibitor to more effectively inhibit insect or nematode gut proteases is completely unknown. Plants, especially when related to the host plant, are poor sources of effective inhibitors, because insects will have evolved protease inhibitor insensitive proteases against these. It is possible to test cysteine protease inhibitors from other sources than plants, but to date no proteinaceous inhibitors of aspartic proteases other than from Solanaceae have been described. The most desirable type of protease inhibitor for pest control of insects utilizing cysteine and/or aspartic proteases for digestion would simultaneously inhibit more than 90% of both activities in insects that have been reared on their host plant in order to specifically target the host plant protease inhibitor insensitive protease complement. Such inhibitors are not known to the art.

It has now been found that cysteine protease inhibitors selected from the group of proteins containing at least one type I repeated thyroglobulin domain are effective in vivo against insects of nematodes utilizing cysteine proteases, and surprisingly it has been found that said inhibitors are particularly active towards insect cysteine proteases which are insensitive to host plant derived cysteine protease inhibitors. Such a property is unprecedented among other types of cysteine protease inhibitors including those of non-plant origin. As a result said inhibitors are highly toxic to for example Colorado potato beetle larvae.

Accordingly in one aspect, the invention relates to a method of protecting a plant or a part of said plant against insect or nematode infestation by one or more insects or nematodes having digestive cysteine proteases, comprising presenting to a locus wherein said insect(s) or nematode(s) is (are) to be controlled an inhibitory amount of a cysteine protease inhibitor selected from the group of proteins containing at least one type I repeated thyroglobulin domain.

Further, it has now been found that some type I repeated thyroglobulin domains can also be effective against aspartic proteases. It is very valuable that the activities against aspartic proteases and cysteine proteases are present on similar structural domains and can be combined in one protein like equistatin, because it is established by the inventors that they act synergistically by more completely inhibiting all insect protease activity.

Accordingly, in a second aspect the invention relates to a type I repeated thyroglobulin domain inhibitor peptide with activity towards aspartic proteases, said peptide having the amino acid sequence extending from amino acid position 68–199 of equistatin of FIG. 1 (SEQ ID NO:2) or a modified type I repeated thyroglobulin aspartic protease inhibitor peptide wherein said modified peptide comprises a peptide having substantial amino acid identity to amino acid position 68–199 of equistatin; truncations of amino acid position 68–199 of equistatin; or truncations of the peptide having substantial amino acid identity to amino acid position 68–199 of equistatin, wherein said modified peptide is functionally equivalent to said amino acid position 68–199 of equistatin with aspartic protease inhibitor activity.

In a third aspect, the present invention relates to an insecticidal or nematocidal composition containing a protein containing at least one type I repeated thyroglobulin domain, wherein the composition is capable of improving the resistance of plant tissue otherwise susceptible to infestation by one or more insects or nematodes having digestive cysteine and/or aspartic proteases.

Accordingly, the invention provides an agricultural, composition containing a carrier and an insect or nematode controlling or combatting amount of a cysteine and/or aspartic protease inhibitor as defined herein.

In a fourth aspect, the invention relates to vectors encoding and capable of expressing a peptide containing one or more type I repeated thyroglobulin domains in a plant cell.

Accordingly, the invention provides a biologically functional expression vehicle containing a promoter effective to promote expression of a downstream coding sequence in plant cells, a DNA coding region coding for the expression in plant cells of protein composed of at least one type I repeated thyroglobulin domain and a termination sequence effective to terminate transcription or translation of the genetic construction product in plant cells, the genetic construction effective to express in the cells of the plant insect controlling amounts of the protein containing at least one type I repeated thryoglobulin domain.

Further the invention provides a method of protecting a plant or a part of said plant against insect or nematode infesctation comprising inserting into the genome of the plant a sequence coding for a protein containing at least one type I repeated thyroglobulin domain with a promoter sequence active in the plant to cause expression of said protein at levels which provide an insect or nematode controlling amount of said protein.

In particular, said method comprises the steps of:
(a) culturing cells or tissues from the plant;
(b) introducing into the cells or tissue at least one copy of a gene coding for the protein containing at least one type I repeated thryoglobulin domain;
(c) regenerating resistant whole plants from the cell or tissue culture.

In a fifth aspect, the invention relates to transformed cells and cell cultures of cells which possess genes encoding a peptide containing one or more type I repeated thyroglobulin domains capable of protecting plant tissue otherwise susceptible to infestation by one or more insects or nematodes having digestive cysteine and/or aspartic proteases.

Further, the invention provides a transgenic plant and its sexual progeny resistant to attack by one or more insects or nematodes having digestive cysteine proteases, said transgenic plant expressing an insect of nematode controlling amount of a protein containing at least one type I repeated thyroglobulin domain.

In sixth aspect, the present invention relates to a process of preparing an insecticidal or nematocidal composition of a peptide containing one or more type I repeated thyroglobulin domains, wherein the composition is capable of improving the resistance of plant tissue otherwise susceptible to infestation by one or more insects or nematodes having digestive cysteine and/or aspartic proteases.

A number of aspects of the present invention are further illustrated in the accompanying drawings, in which FIG. 1 shows the nucleotide sequence and deduced amino acid sequence of SEQ ID NO:1 and SEQ ID NO: 2, respectively, of the equistatin gene from *Actinia equina L.*

FIG. 2 shows a comparison of all three domains of the cDNA encoded amino acid sequence of equistatin of SEQ ID NO:2 and the purified equistatin protein from *Actinia equina L*, showing conservation of the amino acid sequence of SEQ ID NO: 7 with amino acid sequences of SEQ ID NO: 18 through SEQ ID NO:31 of other proteins with type I repeated thyroglobulin domains with known and unknown protease inhibitor activity.

FIG. 5 shows effect of equistatin relative to other cysteine protease inhibitors on in vitro proteolytic activity of the western flower thrips *Frankliniella occidentalis*

Figure 6:
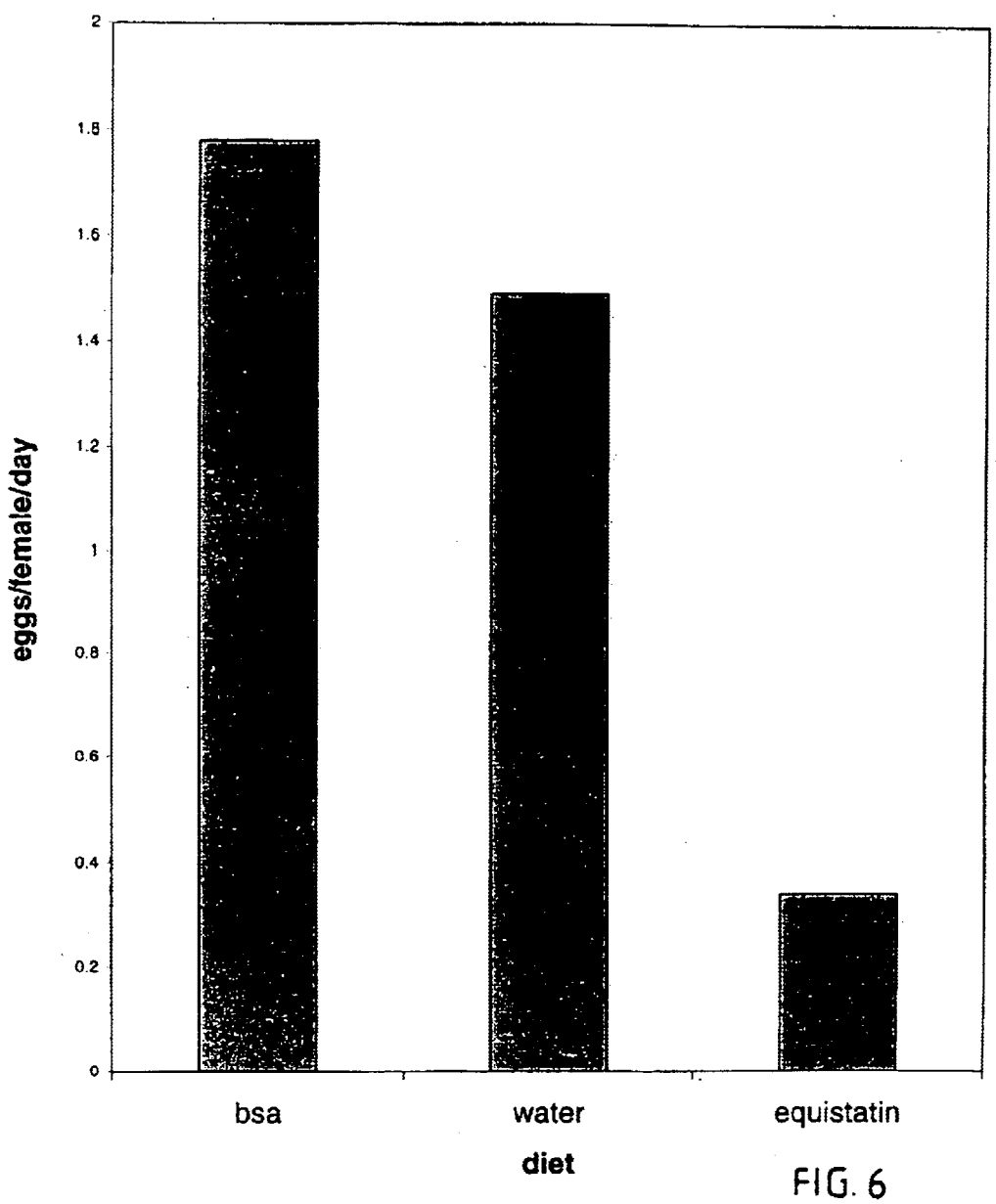
Figure 7:
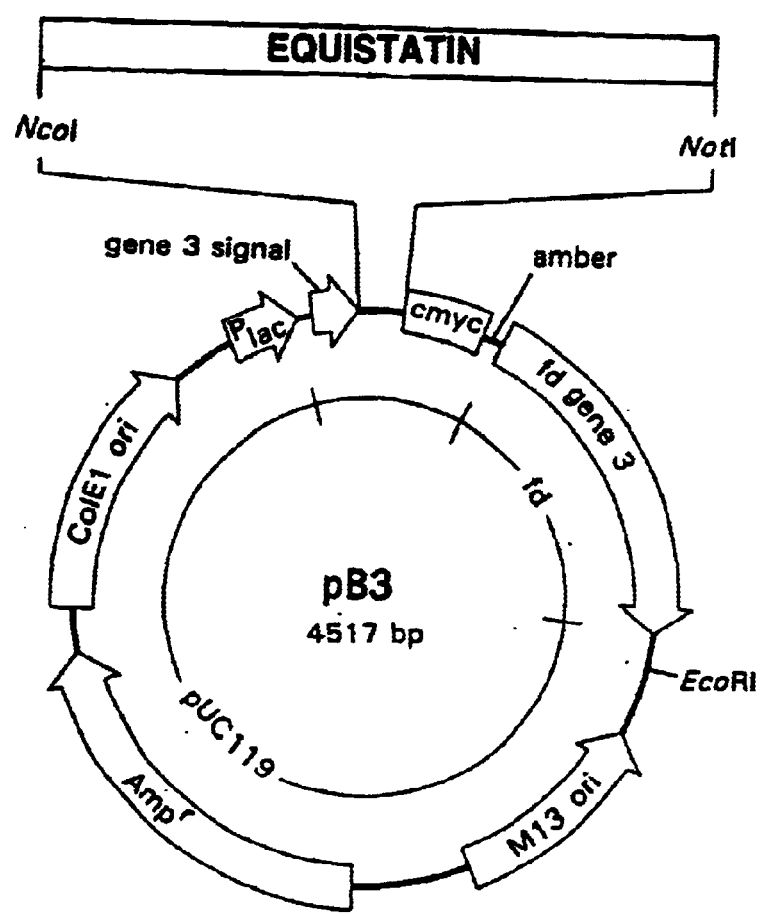
Figure 8:
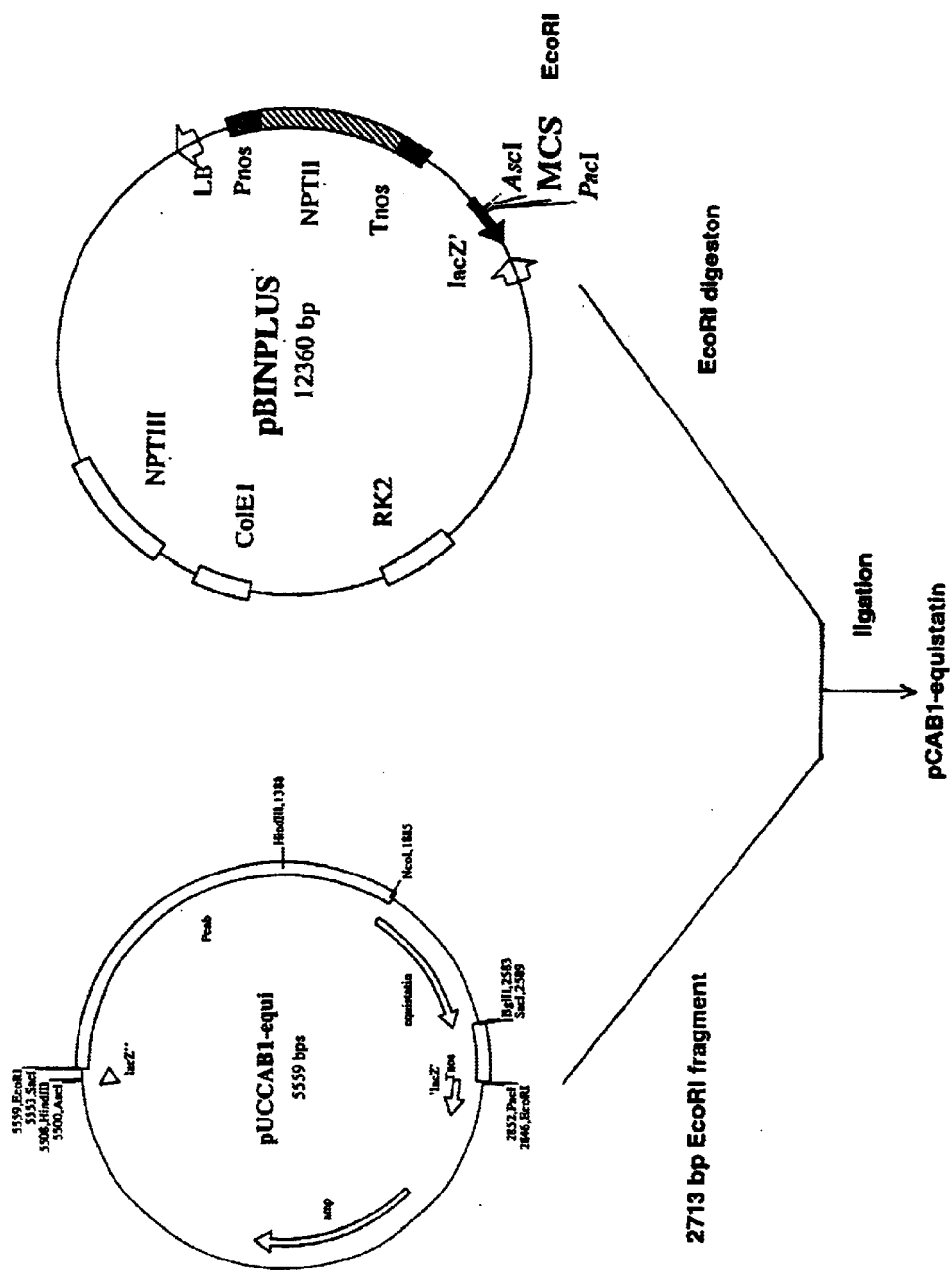
Figure 9:
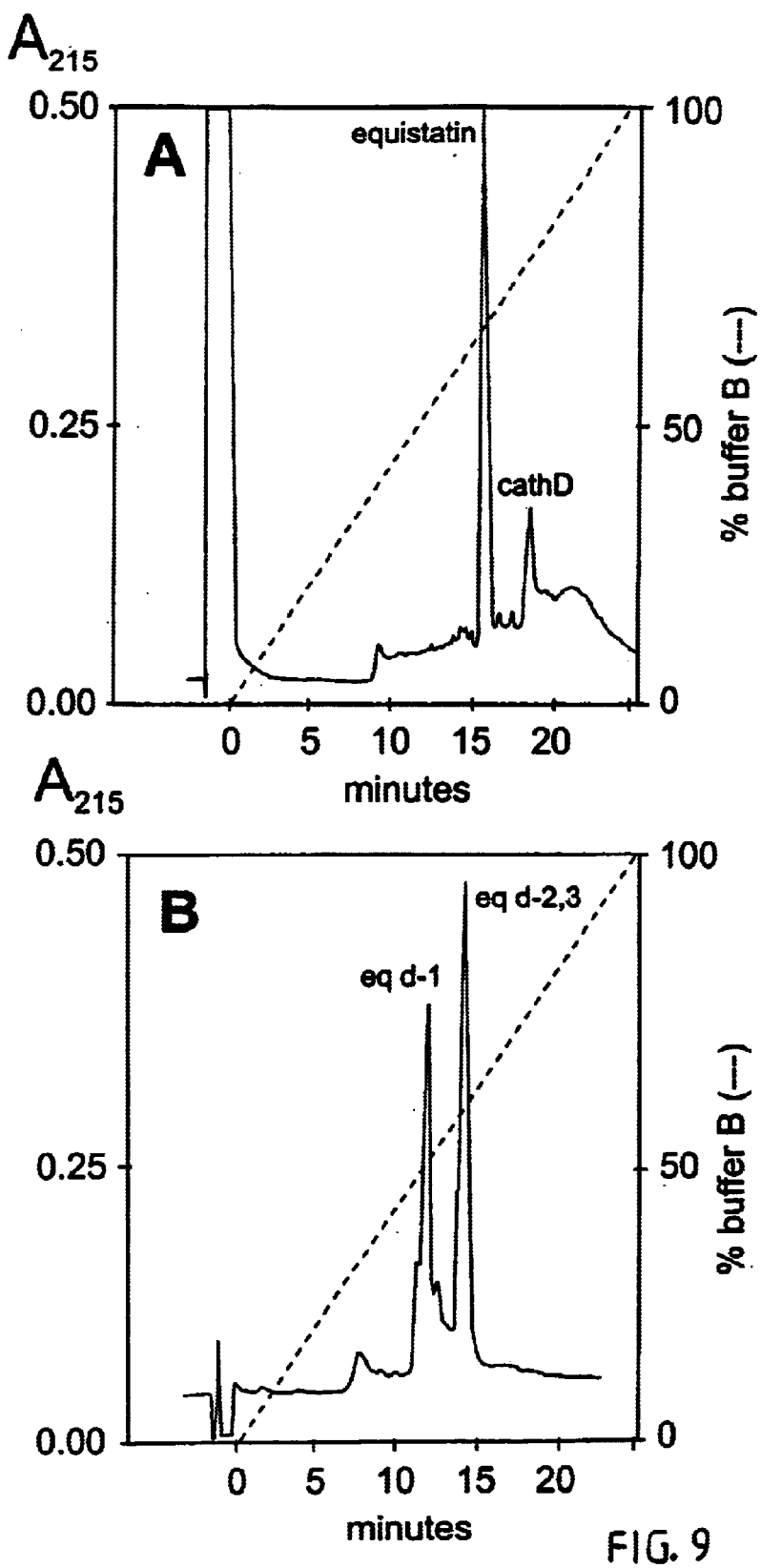

FIG. 6 shows the effect of equistatin on the fecundity of thrips females two days after being placed on a diet containing the inhibitor FIG. 7 shows the plasmid map of pB3-equistatin FIG. 8 shows the construction of the plasmid pCAB1-equistatin FIG. 9 shows HPLC analyses of equistatin. Chromatograms shows the HPLC elution profile of equistatin after incubation with different enzymes. In panel A the equistatin was incubated with cathepsin D in a final molar concentration of 2:1, and in panel B the equistatin was fragmented using 1% (w/w) β-trypsin. Identities of peaks were based on the N-terminal sequences.

Figure 10:
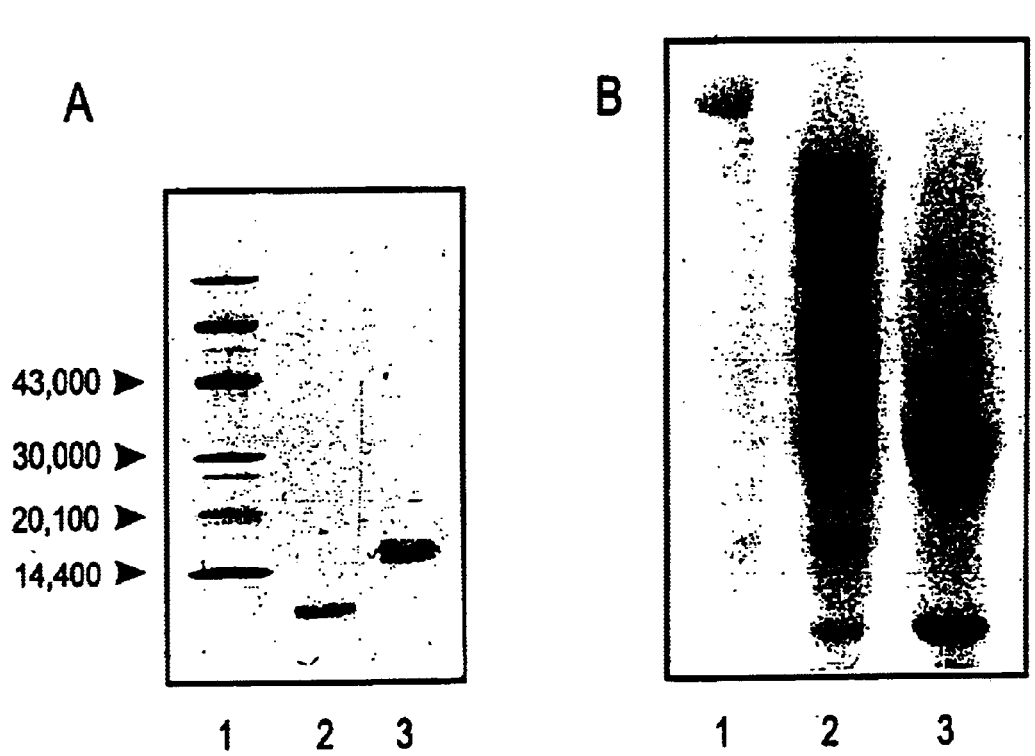

FIG. 10 shows electrophoretic analyses of equistatin. A, SDS-PAGE of dissected equistatin. Lanes: 1, molecular weight standards; 2, first domain of equistatin (eq d-1); 3, the combined second and third domain of equistatin (eq d-2,3). B. Native PAGE of the formation of the equistatin-cathepsin D complex. Lanes. 1, cathepsin D; 2, equistatin and cathepsin D mixed together 30 min before electrophoresis; 3, equistatin. The gels were stained with Coomassie blue.

Figure 11:
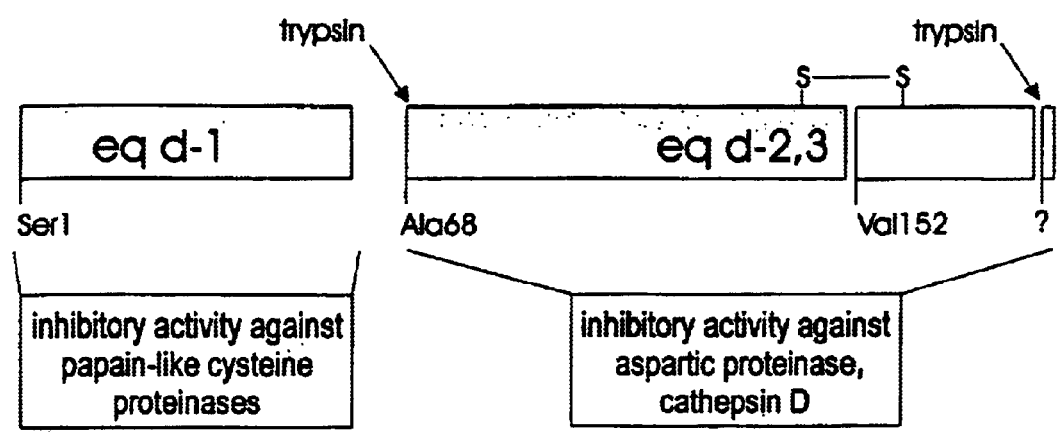

FIG. 11 shows a schematic diagram of the function of equistatin fragments used. Sites of proteolytic cleavages are indicated by gaps and are shown as amino acid numbers. Cleavage sites obtained by the action of β-trypsin are indicated by arrows. The pairing of cysteine residues in disulphide bond is indicated by horizontal line connecting cysteine residues.

Figure 12:
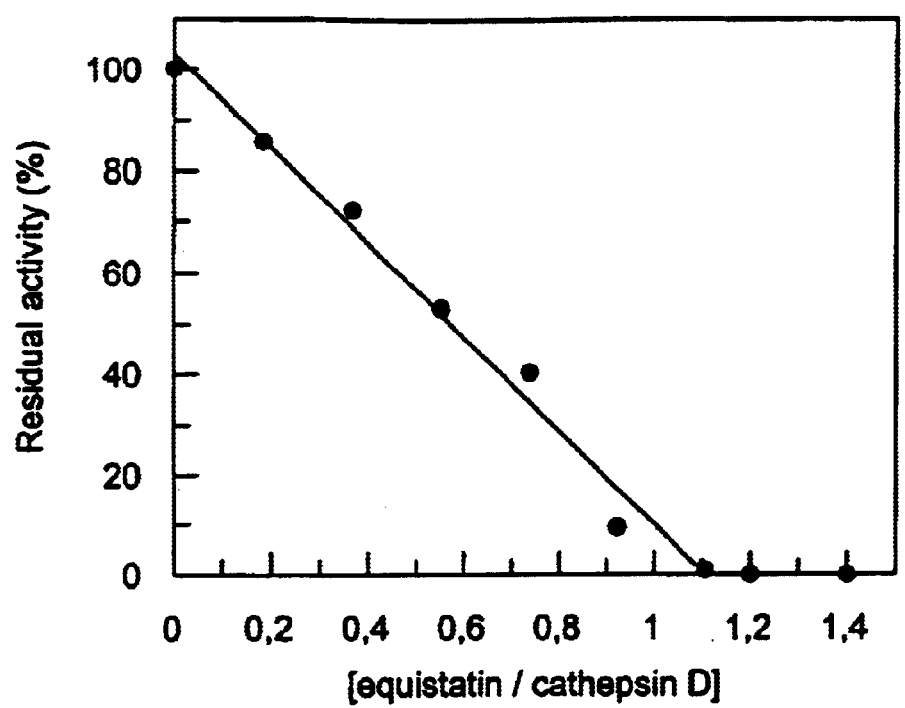

FIG. 12 shows active site titration or equistatin with cathepsin D. Inhibition of 77 nM cathepsin D with increasing concentrations of native equistatin. Residual activity is expressed as percent of control activity in samples containing no inhibitor.

The entire teachings of all references cited herein are hereby incorporated by reference.

It has now been determined that among the type I repeated thyroglobulin domains, domains exist which are active towards aspartic proteases of both human and insect origin. In combination with proteins (P41 invariant chain fragment and equistatin domain I) with domains that are active towards cysteine proteases they have potent inhibitory activity towards "protease inhibitor insensitive" digestive cysteine and aspartic proteases of a broad range of insect species belonging to different insect orders including Colorado potato beetle, thrips, leafminer and corn root-worm. They were larvicidal when administered enterally to the larvae of insects having digestive cysteine and aspartic proteases such as the Colorado potato beetle and strongly reduced the fecundity of thrips which mainly depend on cysteine proteases for the digestion of protein. It is shown that this property of type I repeated thyroglobulin domains is unique among a very broad set of oysteine and aspartic protease inhibitors that were derived from nearly all known types of cysteine and aspartic protease inhibitors. It is shown, therefore, that it is not sufficient, as suggested before, to utilize inhibitors which are at a large evolutionary distance from plants, as these were equally inactive as plant-derived inhibitors. Instead, exclusively the cysteine and/or aspartic protease inhibitors containing the conserved features of a type I repeated thyroglobulin domain were able to fully inactivate the "PI-insensitive cysteine and aspartic proteases" of different insect species. Thus, this invention provides a method for killing insects and nematodes having "protease inhibitor insensitive" digestive cysteine and/or aspartic proteases, including larvae of Colorado potato beetle, comprising administering enterally to the larvae or nematodes a larvicidal or nematocidal amount of protein containing one or more type I repeated thyroglobulin domains depending on whether the insect utilizes one or more classes of protease for digestion.

Definition of Terms

The terms protease inhibitor and proteinase inhibitor are considered equivalent. The term "protease inhibitor insensitive protease" is meant to indicate that such a protease is insensitive to host plant protease inhibitors raised in defense against the attacking pest, but is not meant to exclude that it can be inhibited by protease inhibitors isolated from sources other than the host plant. The terms insect and larva, although not equivalent when used specifically should be understood to include both adult and larval forms of a species when used generically. Thus, the term insect resistance should be understood to include resistance to larval forms as well as adults, and larvicidal materials should be considered insecticidal, particularly since killing larvae produces a corresponding absence of adults.

In a preferred embodiment, the present invention is directed to cysteine/aspartic protease inhibitors from the sea anemone *Actinia equina*, also referred to as equistatin. For purposes of this invention "equistatin" is meant to include a protein encoded by a gene having the sequence set forth in FIG. 1, or a functional derivative thereof. The equistatin peptide that was purified from the sea anemone *Actinia equina* showed the presence of three type I repeated thyroglobulin domains (Lenarcic et al.(1997) *J. Biol. Chem.* 272: 13899; Lenarcic et al. (1998) *J. Biol. Chem.* 273: 12682). Screening a cDNA library from *Actinia equina* with a radiolabeled probe obtained by PCR using two degenerate primers on total cDNA resulted in a clone with a coding sequence containing a signal peptide for secretion and a mature protein part of three domains of nearly identical protein sequence compared to the purified protein primers for the amplification of equistatic cDNA (SEQ ID NO:5 and SEQ ID NO:6, respectively)

EI-deg1: CR (A,C,G,T) AC (A,C,G,T) AA (A,G) TG (T,C) CA (A,G) CA (A,G)

EI-deg2: ATT (A,G) AC (A,G,C,T) TG (A,C,G,T) GG (A,C,G,T) CG (T,C) T—T (A,G) AA

As can be seen from SEQ ID NO: 1 and SEQ ID NO:2 (FIGS. 1 and 2, respectively) the mature protein component of equistatin is composed of 3 domains that appear to have resulted from the duplication of genetic material. On the basis of preliminary cDNA sequence analysis, several structural isoforms of equistatin may occur in the *Actinia equina*. The 3 domains comprise a 22 kD polypeptide. Each domain comprises about 65–68 amino acids, with 3 presumed disulphide bonds. Based on the sequences of the domains, it is apparent that the protein is a member of the conserved type I repeated thyroglobulin domain comprising repeating type I domains. Specifically the domain sequences show high conservation of the amino acid sequence (SEQ ID NO:7): Cys-(Xxx)$_{18-29}$-Pro-Xxx-Cys-(Xxx)$_3$-Gly-(Xxx)$_5$-Gln-Cys-(Xxx)$_6$-Cys-Thr-Cys-Val-(Xxx)$_3$-Gly-(Xxx)$_{10-15}$-Cys. The three domain inhibitors purified from *Actinia equina* was proteolytically cleaved into two major peptides and separated by reverse phase HPLC. Determination of the N-termini of both fragments allowed them to be located in the sequence. One peptide designated eqd-1 consisted of the first domain running from reside 1–67, whereas the second peptide designated eqd-2,3 contained domains 2 and 3 with residues 68–199. The intact equistatin molecule could be inhibited by only 1 papain and 1 Cathepsin D molecule. Inhibition assays with Eqd-1 and Eqd-2,3 determined that Eqd-1 could only be inhibited by papain and Eqd-2,3 only with Cathepsin D. The inhibition constants for the separated domains were similar to the intact equistatin molecule. This demonstrated that, even though these domains appear to be structurally conserved, the specificities for proteases have diverged to completely different classes of proteases. It is not possible with the present evidence to know which residues determine this difference in specificities.

It should be understood that, given the present teachings, one may synthesize or isolate substantially pure functional derivatives of naturally-occurring equistatin molecules. A "functional derivative" of equistatin is a compound which possesses a biological activity that is substantially similar to a biological activity of the equistatin molecule. The term functional derivative is intended to include "fragments", or "effectively homologous variants".

A "fragment" of a molecule is meant to refer to any inhibitory polypeptide subset of a equistatin molecule.

An "effectively homologous variant" of a molecule such as the equstatin molecule is meant to refer to a molecule substantially similar in sequence and function to either the entire molecule of to a fragment thereof. For purposes of this invention, these molecules are identified when they contain the type I repeated thyroglobulin domain. Generally, the effectively homologous sequences should retain high conservation at the naturally occuring positions of the conserved sequence at SEQ ID NO:7: Cys-(Xxx)$_{18-29}$-Val-(Xxx)$_3$-Gly-(Xxx)$_{10.15}$-Cys. The two cysteines on either end of the conserved sequence are conserved, but they do not have conserved positions. They are likely to form structurally important disulphide bridges with any one of the other cysteines, however, for which reason they are included. For purposes of this invention, the structure of one amino acid sequence is effectively homologous to a second amino acid sequence if at least 70 percent, preferably at least 80%, and most preferably at least 90% of the active portions of the amino acid sequence are identical or equivalent. General categories of potentially equivalent amino acids are set forth below, wherein, amino acids within a group may be substituted for other amino acids in that group: (1) glutamic acid and aspartic acid; (2) lysine, arginine and histidine; (3) alanin, valine, leucine and isoleucine; (4) asparagine and glutamine; (5) threonine and serine; (6) phenylalanine, tyrosine and tryptophan; and (7) glycine and alanin. More importantly and critical to the definition, the function of a second amino acid sequence is effectively homologous to another amino acid sequence if the second amino acid conforms to a tertiary structure having the capacity to decrease or eliminate the catalytic activity of a digestive cysteine and/or aspartic protease.

As used herein, the term substantially pure" is meant to describe protein containing at least one type I repeated thyroglobulin domain which is homogeneous by one more purity or homogeneity characteristics. For example, a substantially pure equistatin peptide molecule will show constant and reproducible characteristics within standard experimental deviations for parameters such as molecular weight, chromatographic behaviour and the like. The term, however, is not meant to exclude artificial or synthetic mixtures of the equistatin peptide molecule with other compounds. The term is also not meant to exclude the presence of minor impurities which do not interfere with the biological activity of the equistatin peptide molecule and which may be present, for example, due to incomplete purification. A substantially pure equistatin peptide molecule may be isolated from the source in which it naturally exists by any appropriate protein purification technique. Exemplary techniques include chromatographic techniques, such as gel filtration liquid chromatography, ion exchange chromatography, affinity chromatography, high performance liquid chromatography, reverse phase chromatography or by use of immunological reagents employing anti-equistatin antibodies.

Gene Isolation

It is possible to synthesize in vitro an equistatin peptide from the constituent amino acids (see Merrifield (1963), *J. Amer. Chem. Soc.,* 85:2149–2154; and *Solid Phase Peptide Synthesis* (1969), (eds.) Stewart and Young). The peptides thus prepared may be isolated and purified by procedures well known in the art (see *Current Protocols in Molecular Biology* (1989), (eds). Ausubel, et al. and Sambrook et al., (1989), *Molecular Cloning: A laboratory Manual*).

Although it is possible to determine and synthesize the entire amino acid sequence of the equistatin peptide, it is preferable to isolate the entire sequence of the equistatin gene. DNA encoding an equistatin peptide may be prepared from chromosomal DNA, cDNA or DNA of synthetic origin by using well-known techniques.

Genomic DNA encoding an equistatin peptide may be isolated by standard techniques (Sambrook et al. (1989), supra). Specifically comprehended as part of this invention are genomic DNA sequences encoding allelic variant forms of the equistatin gene, as well as its 5' and 3' flanking regions.

It is also possible to use primers and exponentially amplify DNA in vitro using sequence specified oligonucleotides by the polymerase chain reaction (PCR) (see Mullis et al. (1987), *Meth. Enz.,* 155:335–350; Horton et al. (1989), *Gene,* 77:61; and *PCR Technology: Principles and Applications for DNA. Amplification*, (ed.) Erlich (1989).

cDNA preparations are ligated into recombinant vectors to form a gene library. Alternatively, the cDNAs may be expressed in a vector such as lambda gtll and the library screened using antibodies against the equistatin peptide molecule.

A suitable oligonucleotide, set of oligonucleotides or PCR-derived DNA fragments may be used, by techniques well known in the art, to screen the genomic DNA or cDNA libraries. To facilitate the detection of the desired sequence, the DNA probe may be labeled with any material having detectable physical or chemical property. General procedures for isolating, purifying and sequencing the desired sequences are well known in the art (see Current Protocols in Molecular Biology (1989), supra: and Sambrook et al. (1989), supra).

An alternative way of obtaining a genetic sequence which is capable of encoding the protein containing at least one type I repeated thyroglobulin domain is to prepare it by oligonucleotide synthesis, after the gene sequence of interest is determined (see Caruthers (1983), In: Methodology of DNA and RNA, (ed.) Weissman); Beaucage et al. (1981), *Tetrahedron Letters,* 22: 1859–1962). A series of oligonucleotides may be synthesized in order to provide a series of overlapping fragments which when annealed and ligated will produce both strands or the gene. These fragments are then annealed and ligated together using well known techniques (see Sambrook et al. (1982), supra). Alternatively, the gene may be produced by synthesizing a primer having a so-called "wagging tail", that does not hybridize with the target DNA; thereafter, the genomic sequences are amplified and spliced together by overlap extension (see Horton et al. (1989), Gene, 77:61–68) The resulting DNA fragment with the predicted size is isolated by electrophoresis and ligated into a suitable cloning vector for amplification and further manipulation (see Mullis et al. (1987), supra; and *PCR Technology: Principles and Applications for DNA Amplification*, supra).

Of course, one may incorporate modifications into the isolated sequences including the addition, deletion, or non-conservative substitution of a limited number of various nucleotides or the conservative substitution of many nucleotides, provided that the proper reading frame is maintained. Translational stop and start signals ared added at the appropriate points, and sequences to create convenient cloning sites are added to the ends. Exemplary techniques for modifying oligonucleotide sequences include using polynucleotides-mediated, site-directed mutagenesis (see Zoller et al. (1984), DNA, 3:479–488); Higuchi et al. (1988), *Nucl. Acids Res.,* 16:7351–7367; Ho et al. (1989), supra; and *PCR Technology: Principles and Applications for DNA Amplification*, (ed.) Erlich (1989)).

Gene Expression

In order to further characterize such genetic sequences, it is desirable to introduce the sequence into a suitable host to express the proteins which these sequences encode, and confirm that they possess characteristics of the equistatin peptide molecule. Techniques for such manipulation are well-known in the art and disclosed by Sambrook et al. (1989), supra.

Vectors are available or can be readily prepared for transformation of viruses, prokaryotic or eukaryotic cells.

In general, plasmid or viral vectors should contain all the DNA control sequences necessary for both maintenance and expression of a heterologous DNA sequence in a given host.

Such control sequences generally include a promoter sequence, a transcriptional start or leader sequence, a DNA sequence coding for translation start-signal codon, a translation terminator codon, and a DNA sequence coding for a 3' non-translated region containing a signals controlling termination of RNA synthesis and/or messenger RNA modification. Finally, the vectors should desirably have a marker gene that is capable of providing a phenotypical property which allows for identification of host cells containing the vector, and, in the case of monocot transformation, an intron in the 5' untranslated region, e.g., intron 1 from the maize alcohol dehydrogenase gene that enhances the steady state levels of mRNA.

Exemplary host cells include prokaryotic and eukaryotic organisms. The appropriate procedure to transform a selected host cell may be chosen in accordance with the host cell used. Based on the experience to date, there appears to be little difference in the expression of genes, once inserted into cells, attributable to the method of transformation itself.

Conventional technologies for introducing biological material into host cells include electroporation [see Shigekawa and Dower (1988), *Biotechniques*, 6:742; Miller, et al. (1988), *Proc. Natl. Acad. Sci. USA*, 85:856–860; and Powell, et al (1988), *Appl. Environ Microbiol.*, 54:655–660); direct DNA uptake mechanisms (see Mandel and Higa (1972), *J. Mol. Biol.*, 53:159–162; Dityatkin, et al. (1972), Biochimica et Biophysica Acta, 281:319–323; Wigler, et al. (1979), Cell, 16:77; and Uchimiya, et al. (1982), In: *Proc. 5th Intl. Cong. Plant Tissue and Cell Culture*, A. Fujiwara (ed.), Jap. Assoc. for Plant Tissue Culture, Tokyo, pp. 507–508); fusion mechanisms (see Uchidax, et al. (1980), In: *Introduction of Macromolecules Into Viable Mammalian Cells*, C. Baserga, G. Crose, and G. Rovera (eds.) Wistar Symposium Series, Vol. 1, A. R. Liss Inc., NY, pp. 169–185]; infections agents [see Fraley, et al (1986), *CRC Crit. Rev. Plant Sci.*, 4:1–46); and Anderson (1984), Science, 226:401–409]; microinjection mechanisms [see Crossway, et al (1986), *Mol. Gen. Genet.*, 202:179–185] and high velocity projectile mechanisms [see EPO 0 405 696].

Transformants are isolated in accordance with conventional methods, usually employing a selection technique, which allows for selection of the desired organisms as against unmodified organisms. Generally, after being transformed, the host cells are grown for about 48 hours to allow for expression of marker genes. The cells are then placed in selective and/or screenable media, where untransformed cells are distinguished from transformed cells, either by death or a biochemical property. The selected cells can be screened for expression of the equistatin peptide molecule or functional derivatives thereof by assay techniques such as immunoblot analysis, inhibitory activity assay, enzyme-linked immunosorbent assay, radioimmunoassay, or fluorescence-activated cell sorter analysis, immunohistochemistry and the like. The transformed tissues are then tested for insect controlling activity.

A host cell may be transformed to provide a source from which significant quantities of the vector containing the gene of interest can be isolated for subsequent introduction into the desired host cells or for which significant quantities of the protein may be expressed and isolated. Exemplary recombinant host cells include unicellullar prokaryotic and eukaryotic strains. Prokaryotic microbes that may be used as hosts include *Escherichia coli*, and other *Enterobacteriaceae, Bacilli*, and various *Pseudomonas*. Common eukaryotic microbes include *Sacchromyces cerevisiae* and *Pichia pastoris*. Common higher eukaryotic host cells include Sp2/0 or CHO cells. Another preferred host is insect cells, for example *Drosophila* larvae, in which the vector contains the *Drosophila* alcohol dehydrogenase promoter.

Alternatively, baculovirus vectors, e.g., *Autographa californica* nuclear polyhedrosis virus (see Miller et al. (1983), *Science*, 219:715–721) may be engineered to express large amounts of the equistatin peptide molecule or functional derivatives thereof in cultured insects cells (see Andrews et al. (1988), *Biochem J.*, 252:199–206.

Agricultural Composition

The present invention provides an agricultural composition for application to plants or parts thereof which are susceptible to infestation by insects or nematodes having digestive cysteine proteases, said agricultural composition comprising an protein containing at least one type I repeated thyroglobulin domain. Often the agricultural composition will contain an agriculturally acceptable carrier. By the term "agriculturally acceptable carrier" is meant a substance which may be used to dissolve, disperse or diffuse an active compound in the composition without impairing the effectiveness of the compound and which by itself has no detrimental effect on the soil, equipment, crops or agronomic environment.

The agricultural compositions may be applied in a wide variety of forms including powders, crystals, suspensions, dusts, pellets, granules, encapsulations, microencapsulations, aerosols, solutions, gels or other dispersions. In addition to appropriate liquid or solid carriers, compositors may include adjuvants, such as emulsifying and wetting agents, spreading agents, dispersing agents, adhesives or agents which stimulate insect feeding according to conventional agricultural practices. Adjuvants for the formulation of insecticides are well known to those skilled in the art.

The concentration of protein containing at least one type I repeated thyroglobulin domain will vary widely depending upon the nature of the particular formulation, particularly whether it is a concentrate or it is to be used directly. The protein containing at least one type 1 repeated thyroglobulin domain generally will be present in at least 1 percent by weight and may be up to 100 percent by weight.

The presentation of the agricultural composition may be achieved by external application either directly or in the vicinity of the plants or plants parts. The agricultural compositions may be applied to the environment of the insect pest(s), e.g., plants soil or water, by spraying, dusting, sprinkling, or the like.

The present invention further contemplates using recombinant hosts (e.g., microbial hosts and insect viruses) transformed with a gene encoding the protein containing at least one type I repeated thyroglobulin domain and applied on or near a selected plant or plant part suceptible to attack by a target insect. The hosts are selected capable of colonizing a plant tissue suceptible to insect infestation or of being applied as dead or non-viable cells containing the protein containing at least one type I repeated thyroglobulin domain. Microbial hosts of particular interest will be the prakaryotes and the lower eukaryotes, such as fungi.

Characteristics of microbial hosts for encapsulating an protein containing at least one type I repeated thyroglobulin domain include protective qualities for the protein, such as thick cell walls, pigmentation, and intracellular packaging or formation of inclusion bodies; leaf affinity; lack of mammalian tonicity; attractiveness to pests for ingestion; ease of killing and fixing without damage to the protein containing at least one type I repeated thyroglobulin domain; and the ability to be treated to prolong the activity of the protein containing at least one type I repeated thyroglobulin domain. Characteristics of microbial hosts for colonizing a plant include non-phytotoxicity; ease of introducing a genetic sequence encoding an protein containing at least one type I repeated thyroglobulin domain, availability of expression systems, efficiency of expression and stability of the insecticide in the host.

Illustrative prokaryotes, both Gram-negative and positive, include *Enterobacteriaceae*, such as *Escherichia; Bacillaceae; Rhizoboceae*, such as *Rhizobiun and Rhizobacter; Spirillaceae* (such as *photobacterium*) *Zymomonas, Serratia, Aeromonas, Vibrio, Desulfovibrio, Spririllum, Lactobacillaceae; Pseudoinonadaceae*(such as *Pseudomonas and Acetobacter*) *Azotobacteriaceae* and Nitrobacteriaceae. Among eukaryotes are fungi (such as *Phycomycetes* and *Ascomycetes*), which includes yeast (such as *Saccharomyces* and *Schizosaccharomyces*); and *Basidiomycetes* yeast (such as *Rhodotorula, Aureobasidium, Sporobolomyces*) and the like.

The present invention also contemplates the use of a baculovirus containing a gene encoding an protein containing at least one type I repeated thyroglobulin domain. Baculoviruses including those that infect *Heliothis virescens* (cotton bollworm), *Orgyla psuedocsugata* (Douglas fir tussock moth), *Lymantria dispar* (gypsy moth), *Autographica californica* (Alfalfa looper), *Neodiprion serfiter* (European pine fly) and *Laspeyresia pomonella* (coddling moth) have been registered and used as pesticides (see U.S. Pat. No. 4,745,051 and EP 175 852).

The recombinant host may be formulated in a variety of ways. It may be employed in wettable powders, granules or dusts, or by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other insecticidial additives surfactants, and bacterial nutrients or other agents to enhance growth or stabilize bacterial cells. Liquid formulations may be aqueous-based or non-aqueous and employed as foams, gels, suspensions, emulsifiable concentrates, or the like. The ingredients may include Theological agents, surfactants, emulsifiers, dispersants, or polymers.

Transgenic Plants

Alternatively, the protein containing at least one type I repeated thyroglobulin domain can be incorporated into the tissues of a susceptible plant so that in the course of infesting the plant the insect consume insect-controlling amounts of the selected protein containing at least one type I repeated thyroglobulin domain. This method offers particular advantages to reach plant tissues digested by insects or nematodes that are normally very hard to reach by conventional application of pesticides. In addition, there are important economical and environmental benefits to be gained when the need to apply pesticides can be reduced.

The method also offers advantages when the potential for insects becoming resistant is considered. Heavy application of insecticidal materials generally to a field or a geographical area by dust or spray or by soil incorporation tends to impose strong selection pressures, since insects have no "safe havens" where non-resistant individuals can survive. However, many insect pests of crop plants also attack non-crop species. Limiting the insecticidal materials to the crop plants in the region by expressing the insecticidal materials only in those plants permits continued survival of non-resistant insects in associated weed plants which provide nor only "safe havens" from the toxic compound but food for the insects. This reduces slection pressure significantly and this slows development and spread of resistant insects.

This method also offers advantages from the standpoint of soil and groundwater contamination, since no application vehicle is required. The insecticidal components themselves are of natural origin and break down naturally when the plant is digested or decomposes. The method offers further advantages from the standpoint of cost, since no application expense is involved and the cost of the insecticidal materials is factored into the price of the seed or other reproductive material which the grower purchases.

One method of doing this is to incorporate the protein containing at least one type I repeated thyroglobulin domain in a non-phytotoxic vehicle which is adapted for is systemic administration to the susceptible plants. However, since the genes which code for protein containing at least one type I repeated thyroglobulin domain may be isolated, the invention contemplates, in a preferred embodiment, transgenic plants which are capable of biologically synthe-sizing proteins containing at least one type I repeated thyroglobulin domain to provide the plants with a new, or an additional, mechanism of protection against attack by insects or nematodes.

The invention provides methods of imparting resistance to insect infestation by insects having digestive cysteine and/or aspartic proteases to plants of a susceptible taxon, comprising: (a) culturing cells or tissues from at least one plant from the taxon; (b) introducing into the cells of the cell or tissue culture a structural gene encoding an protein containing at least one type I repeated thyroglobulin domain operably linked to plant regulatorv sequences which cause expression of the gene in the cells, and (c) regenerating insect-resistant whole plants from the cell or tissues culture.

The expression of uniquely high quantities of proteins containing at least one type I repeated thyroglobulin domain may be deleterious to the plant itself. The use of signal sequences to secrete or sequester in a selected organelle allows the protein to be in a metabolically inert location until released in the gut environment of an insect pathogen.

The DNA sequence will generally be one which orginates from, or has substantial sequence homology to an protein containing at least one type I repeated thyroglobulin domain, originating from an organism different from that of the target organism.

Optimal Expression in Plants

In order to optimize the transcriptional and translational efficiency of such systems, it is possible examine the frequency of codon usage and determine which codons are, in essence, preferred within the transcriptional and translational systems normally present in that plant. Using such preferred usage codons, it is possible to construct a protein coding sequence which may result in a significantly enhanced level of transcriptional and translational efficiency of the equistatin gene or a functional derivative of that gene compared to what would be achieved by taking the coding sequence directly in an ummodified form of the donor organism. In addition the coding sequence may be optimized further by removing potential plant poly-adenylation signals, cryptic splicing sites and MPNA instability motifs as was shown for *Bacillus thuringiensis* toxin genes.

Generally, the insertion of heterologous genes appears to be random using any transformation techniaue; however, technology currently exists for producing plants with site specific recombination of DNA into plant cells (see WO/910–9957). The activity of the foreign gene inserted into plant cells is dependent upon the expression characteristics of the individual inserted genes, resulting from control regions (promoters, poly-adenylation regions, enhancers, etc.) and from the influence of endogenous plant DNA adjacent the chimeric insert and by the copy number.

The promoter selected should be capable of causing sufficient expression to result in the production of an insect controlling amount of protein. Suitable promoters may include both those which are derived from a gene which is natually expressed in plants and synthetic promoter sequences which may include redundant or heterologous enhancer sequences. A number of promoters which are active in plant cells include the nopaline synthase, octopine synthase and mannopine synthase promoters from the tumor-inducing plasmids of *Agrobacterium tumefaciens*. The present invention contemplates constitutive promoters such that the transformed plant has increased tolerance to insect pests. Examples of constitutive promoters include the CaMV 19S and 35S promoters (JP 63287485), ubiquitin promoter, the rice actin promoter (WO/9109948).

In species which produce a native protein containing at least one type I repeated thyroglobulin domain which is not produced in or not distributed to tissues whLch are normally infested with the insects, a tissue specific promoter can be used to provide localized expression of or overproduction of the protein containing at least one type I repeated thyroglobulin domain. Examples of tissue specific promoters include the root specific promoters such as maize metallothioneirn (EP 452269), the root specific promoter (WO/9113992) the plant seed storage body promoter (WO/9113-993), and the alcohol dehydrogenase-1 promoter. Promoters known to be light inducible include the promoter of the gene encoding the small subunit (ss) or the ribulose-1,5-bisphosphate carboxylase from soybean and the promoter of the gene encoding the chlorophyll a/b binding protein in greening leaves (Coruzzi et al., (1983), *J. Biol. Chem.*, 258:1399; aand Dunsmuir, et al. (1983), *J. Molecular andADD. Gen.*, 2:285; Nap et al. (1993) Plant Molec, Biol. 23: 605–612.

Finally, a wound or pathogen inducible promoter can be used co provide expression of the proteins containing at least one type I repeated thyroglobulin domain when a tissue is attacked by a plant pest. Examples of wound or pathogen inducible promoters include the proteinase inhibitor II promoter.

Plant Vectors

Suitable vectors for transforming plant tissue and protoplasts have been described in the literature and are set forth herein (see deFrammond et al. (1983), Biotechnology, 1: 262; An et al. (1985), *EMBO J.* 4: 277; Potrykus et al. (1985), *Mol. Gen. Genet.* 199: 183; Rothstein et al 1987), *Gene,* 53: 153; WO 90/08829 and WO 84/02913; and, in a preferred embodiment, pCAB1 (as described in che Examples). It is not necessary in practice that the vector harboring the selectable marker gene also contain the gene of interest. Rather, co-transformation of such vectors may be used to transform plant cells.

Transformation Procedure

The appropriate procedure to produce mature transgenic plants may be chosen in accordance with the plant species used. Regeneration varies from species to species of plants. Efficient regeneration will depend upon the medium, on the genotype and on the history of the culture. Once whole plants have been obtained, they can be sexually or clonally reproduced in such a manner that at least one copy of the sequence is present in the cells of the progeny of the reproduction. Such procedures may be chosen in accordance with the plant species used.

Breeding Transgenic Plants

Mature plants, grown from the transformed plant cells, may be selfed to produce an inbred plant. In diploid plants, typically one parent may be transformed and the other parent may be the wild type. The parent will be crossed to form first generation hybrids ($F_1$), which are selfed to produced second generation hybrids ($F_2$). $F_2$ hybrids with the genetic makeup of the protein containing at least one type I repeated thyroglobulin domain are chosen and selfed to produce an inbred plant.

Conventional plant breeding methods can be used to transfer the equistatin structural gene or a functional derivative thereof via crossing and backcrossing. Such methods comprise the further steps of (a) sexually crossing the insectresistant plant with a plant from the insect-susceptible variety; (b) recovering reproductive material from the progeny of the cross; and (c) growing insect-resistant plants from the reproductive material. Where desirable or necessary, the agronomic characteristics of the susceptible variety can be substantially preserved by expanding this method to include the further steps of repetitively (d) backcrossing the insect-resistant progeny with insectsusceptible plants from the susceptible variety; and (e) selecting for expression of insect resistance (or an associated marker gene) among the progeny of the backcross, until the desired percentage of the characteristics of the susceptible variety are present in the progreny along with the gene imparting insect resistance. Subseauently, the inbreds according to this invention may be crossed with another inbred line to produce the hybrid.

Potentiatiors

The present invention further contemplates using, with the protein containing at least one type I repeated thyroglobulin domain, adjuvants, chemical or biological additives in an effort to expand the spectrum or targeted pests, to extend the duration of effectiveness of the protein containing at least one type I repeated thyroglobulin domain or to help stabilize the agricultural composition of the protein containing at least one type I repeated thyroglobulin domain.

Exemplary potentiators would include lectins, amphipathic proteins or complementary protease inhibitors. For example, the presence of more than one defensive protein, in the presence of other defensive proteins, may have an important role in the plant defense against insect attacks. It is known that *Hemiptera* and *Coleoptera* insects developed alternative pathways of protein digestion of foods containing high levels of certain protease inhibitors it may be advantagous to include inhibitors from families such as the Cystatins (Type I to III and the phytocvstatins), Kunitztype inhibitors, Virgiferin inhibitors, Bowman-Birk inhibitors, Barley Trypsin inhibitors, Potato inhibitors I and II, Squash inhibitors, Ragi 1–2/Maize bifunctional inhibitors, carboxypeptidase A and B inhibitors and aspartic protease inhibitors (see Ryan (1990), *Annu. Rev. Phytopathol.,* 28:425–49.

Insects and Nematodes

The present invention contemplates protecting any plant of a taxon which is susceptible to infestation and damage by insects or nematodes having digestive cysteine and/or aspartic proteases. Such insect pests include in particular Coleopteran insects of the families Tenebrionidae, Curculionidae, Bruchidae and Chrysomelidae, Thysanopteran insects and Dipteran insects. Such plant parasitic nematodes include *Globodera* pallida, *Heterodera schachtii* and Meloidogyne incognita. Mention is made of insects of especially *Leptinotarsa decemlineata, Frankliniella occidentalis, Diabrotica virgifera* and *Liriomyza trifolii* commonly referred to as the Colorado potato beetle, Western flower thrips, western corn rootworm and leafminer. Other specific insects include southern corn rootworm, Mexican been beetle, red flour beetle, confused flour beetle, cowpea beetle, boll weevil, rice weevil, maize weevil, granary weevil, lesser grain borer, flea beetles, Egyptian alfalfa weevil, bean weevil, yellow mealworm, asparagus beetle, squash bug. By the term "taxon" herein is meant a unit, a botanical classification of genus or lower. It thus includes genus, species, cultivars, varieties, variants and other minor taxonomic groups which lack a consistent nomenclature.

Plants

Exemplary plants include potato, maize, tomato, sorghum, cotton, soybean, dry beans, rape, alfalfa, asparagus, sweet potato and chrysanthemum. However, it is not to be construed as limiting, in as much as these insects may infest certain other crops. Thus, the methods of the invention are readily applicable to numerous plant species, if they are found to be susceptible to the plant species listed hereinabove, including without limitation, species from the genera *Medicago, Trifolium, Vigna, Citrus, Daucus, Arabidopsis, Brassica, Raphanus, Sinapis, Capsicum, Lycopersicon, Nicotiana, Solanum, Helianthus, Bromus, Asparagus, Panicum, Pennisetum, Cucumis, Glycine, Lolium, Triticum* and *Zea*.

EXAMPLES

The present invention is illustrated in further detail by the following examples. The examples are for the purposes of illustration only, and are not to be construed as limiting the scope of the present invention. All DNA sequences are given in the conventional 5' to 3' direction. All amino acid sequences are given in conventional amino terminus to carboxylic acid terminus direction in carrying out the following examples, all DNA manioulations were done according to standard procedures, unless otherwise indicated. See Sambrook et al. (1989), *Molecular Cloning: A Laboratory Manual*, published by Cold Spring Harbor Laboratory (U.S.A.)

Example 1

Activity of Domain 2–3 of Equistatin Towards Cathepsin D Type Aspartic Proteases.

Equistatin was isolated from sea anemone *A. equina* by a procedure that was described previously utilizing its inhibitory activity toward cysteine proteinase, papain (Lenarcic et al. (1997) J. Biol. Chem. 272: 13899). Besides cysteine proteinases, equistatin was screened for the inhibition of two other classes of proteinases, aspartic proteinases (cathepsin D) and serine proteinase (trypsin). The inhibitory effect of equistatin was observed only when it was reacting with cathepsin D. The obtained inhibition was unexpected since equistatin is known as a strong inhibitor of papain-like cysteine proteinases. In addition, it was reported that p41 fragment does not have any inhibitory effect on cathepsin D (Bevec et al. (1996) J. Exp. Med. 183: 1331–1338). To ascertain that equistatin does not act as a substrate for cathepsin D we incubated both in different molar concentrations for different period of time and the mixtures subjected on the reverse-phase HPLC system (FIG. 9A). No degradation products were observed for cathepsin D. On the contrary, equistatin was found to be a good substrate for trypsin and this fact was used for the separation of thyroglobulin type-1 domains by a limited proteolysis with β-trypsin. 500 μg equistatin was incubated with 5 μg of β-trypsin in 0.5 ml of 0.1 M Tris/HCl buffer pH 8.0, for 40 min at 37° C. Reaction was stopped by the addition of trifluoroacetic acid. The 9-trypsin digest of equistatin was separated by high performance liquid chromatography (Milton Roy Co.) using a reverse phase Vydac C18 column equilibrated with 5% acetonicril containing 0.1% (v/v) trifluoroacetic acid. Elution was performed using a linear gradient of 80% (v/v) acetonitrile containing 0.1% (v/v) trifluoroacetic acid. Absorbance was monitored at 215 nm. Two major peaks were obtained on the reverse-phase. HPLC (FIG. 9B). The molecular weights, estimated by the SDS PAGE under non-reducing conditions, were about 7,000 and 14,000 (FIG. 10). Determination of the N-termini of the both fragments allowed them to be located in the sequence of the equistatin molecule shown schematically in FIG. 11. The C-termini of the fragments were not identified directly, but their size, as indicated by SDS PAGE, were consistent with their being a single and a double domain. The smaller fragment starts with the N-terminus of the equistatin and therefore corresponds to the first domain (eq d-1). The larger fragment revealed two sequences, starting with Ala68 and Val152. The Lys67-Ala68 bond is positioned in the beginning of the second domain, while the cleavage of the Arg151-Val152 bond was not the result of the limited proteolysis (FIG. 11). It was reported that isolated equistatin is substantially nicked between Arg151 and Val152, the chains are disulfide bonded and go apart only after reduction (Lenarcic et al. (1997) J. Biol. Chem. 272: 13899–13903). A narrow double band, visible on SDS PAGE, is most likely the result of the fragmentation very near to the C-terminus, meaning that this fragment represents the combined second and the third domain, eq d-2,3. According to the sequence data the three sequentially homologous parts of equistatin may have three potential proteinase binding sites. In previous work it was shown that the binding stoichiometry of equistatin and papain, as the representative of cysteine proteinases, is 1:1 (Lenarcic et al. (1997) J. Biol. Chem. 272: 13899). When aspartic proteinase, cathepsin D, was titrated with equistatin it was estimated that again 1 mol of equistatin was needed for the saturation of 1 mol of cathepsin D (FIG. 12). This value was independent over a wide concentration range. In order to investigate the inhibitory activities of individual domains of equistatin a detailed kinetic analysis of the inactivation of papain and cathepsin D was performed. All kinetic and equilibrium constants are given in Table 2. The first domain, eq d-1, exhibited practically the same inhibitory characteristics against papain as intact equistatin, p41 fragment or ECI. This group of thyroglobulin type-1 domain inhibitors are considered as competitive, reversible and tight binding inhibitors of cysteine proteinases, as papain, cathepsins B and L and cruzipain. The two-domain inhibitor, eq d-2,3, showed practically no inhibition of papain.

The kinetics of binding of equistatin to cathepsin D was performing using a synthetic substrate which contains a chromophore, such as a nitrophenylalanine residue, in the P1' position. The assay sensitivity, afforded by H-Pro-Thr-Glu-Phe*Nph-Arg-Leu-OH (SEQ ID NO:8) as substrate, alowed us to use 6.4 nM concentration of the enzyme as a minimal concentration in the test. The obtained equilibrium dissociation constant for the interaction between cathepsin D and equistatin ($K_i$=0.3 nM) indicates that equistatin is a remarkably good inhibitor of aspartic proteinase, cathepsin D. For the papain active fragment, eq d-1, the $K_i$ approx. 1 mM was determined. This value is several orders of magnitude higher than is the $K_i$ value for the intact equistatin, indicating that the inhibitory active site of the equistatin must be located on other domains. The eq d-2,3 indeed exhibited practically the same inhibition characteristics as the whole equistatin (Ki>0.6 nM). Additionally, the formation of a tight complex between cathepsin D and equistatin was also visualized by a native PAGE (FIG. 10B).

Equistatin is the first protein inhibitor of cathepsin D with known primary structure of animal origin. Until now only derivatives of pepstatin were known to be as strong inhibitors of cathepsin D as is equistatin.

The data provided in this study clearly show that different thyroglobulin type-1 domains present in equistatin, despite their extensive amino acid sequence similarity, target different classes of proteinases, either cysteine or aspartic proteinase cathepsin D.

TABLE 2

Kinetic constants for the interaction of equistatin, eq d-1 and eq d-2, 3 with papain and cathepsin D

| Enzyme | Inhibitor | $10^{-6} \times k_a$ $M^{-1} s^{-1}$ | $10^4 \times k_d$ $s^{-1}$ | $K_i$ nM |
|---|---|---|---|---|
| papain[a] | equistatin | 12 ± 0.6 | 65 ± 1.5 | 0.57 ± 0.04 |
| | eq d-1 | 1.8 ± 0.35 | 11 ± 0.3 | 0.61 ± 0.01 |
| | eq d-2, 3 | ND[d] | ND | >1000[e] |
| cathepsin D[b] | equistatin | ND | ND | 0.3 ± 0.16 |
| | eq d-1 | ND | ND | >1000[e] |
| | eq d-2, 3 | ND | ND | 0.4 ± 0.15 |

[a]Continuous rate assay was used for kinetic analysis of the interaction of papain with inhibitors. Ki was calculated from the ratio $k_d/k_a$.
[b]Data were determined from the inhibitory effect of inhibitor on the steady state. velocity for cathepsin D-catalysed hydrolysis of chromophoric substrate.
[d]Not determined.
[e]Neither eq d-2, 3 showed significant influence on papain nor eq d-1 on cathepsin D even at 5 mM; thus inhibition constant were estimated to be greater than 1 mM.

Example 2
Molecular Cloning of Equistatin

From a single specimen of sea anemone *Actinia equina L.*, total RNA was isolated by disrupting the tissue in a liquid nitrogen. Two grams of ground, deeply frozen tissue was transferred into 20 ml of guanidinium thiocyanate solution (5.5 M GTC, 0.5 M EDTA, 0.2 M β-mercapto-ethanol) and homogenized in an electrical mixer (16,000 rpm, 4×30 sec.). Subsequently, the solution was centrifuged at 6000×g, 20 mm. at 15° C. 10 ml of clear supernatant was transferred to 10 ml of Cesium TFA solution (ρ=1.5 mg/ml), supplemented with 2.5 ml of 0.5 M EDTA, pH=8.0. Sample was centrifuged for 24 h at 125,000×g, 15° C. The supernatant was removed and total RNA (pellet) was dissolved in 1 ml of proteinase K solution (0.5 mg/ml). After incubating the solution at 50° C., ½ h, total RNA was precipitated by ¹⁄₁₀ volume of 3 M KOAc, pH=5.2 and 2.5 vol. of 96% ethanol and the mixture was placed overnight in the freezer at −20° C. Total RNA was pelleted at 8000× g and the pellet was dissolved in 2 ml of TE buffer. 1 ml of dissolved sample was heated at 65° C. for 5 mm, cooled on ice and subsequently, 0.2 ml of TE buffer, supplemented with 3M NaCl was added. Whole sample was applied to the top of the oligo (dT)—cellulose bed in the column. The cellulose was washed three times with the TE buffer, supplemented with 0.5 M NaCl and 0.1 M NaCl, respectively. Poly(A)+RNA was eluted with 1 ml (divided into 4 aliquots of 0.25 ml) of TE buffer, prewarmed to 65° C. One third of the sample (approx. 1 μg) was used for a synthesis of cDNA according to manufacturer's procedure (Amersham). First strand cDNA synthesis was performed using 11 μl of mRNA solution, 4 μl 5 X reaction buffer, 1 μl Na-pyrophosphate solution, 1 μl human placental ribonuclease inhibitor (5 U/μl), 2 μl of dNTP mix solution and oligo dT primer solution (1 μl). After addition of 2 μl (10 U/μl) of reverse transcriptase, a mixture was incubated at 42° C. for 40 minutes. Second strand cDNA was synthesized by adding the following components: 37.5 μl of second strand reaction buffer, 7 μl of *E. coli* DNA polymerase 1 (4U/μl) and 1 μl of E. coli ribonuclease H (1U/μl). The reaction mix was incubated sequentially at 12° C. for 60 minutes and 22° C. for 60 minutes. After heat denaturation (5 minutes at 70° C.), 0.5 μl of T4 DNA polymerase (2U/μl) was added and the reaction mix was incubated at 37° C. for 10 minutes. 2.5 μl (250 pmoles) of EcoRI-adaptors were ligated to 1 μg of cDNA, using 2 μl of T4 DNA ligase (4U/μl) in 20 μl of ligation mixture. After 8 h at 16° C., the ligation mixture was subjected to column purification/size fractionation of adaptor-linked cDNA, using spun columns and TE buffer. Collected fractions of purified cDNA were phosphorylated by T4 polynucleotide kinase (8U/μl) and cDNA was ligated into dephosphorylated λgtll bacteriophage arms using T4 DNA ligase (40U/μg DNA). Finally, whole ligation mixture was in vitro packaged using packaging extract from the same manufacturer (Amersham). A portion of λgtll cDNA library ($10^5$ pfu) was used for the infection of Y1090 *E. coli* cells and mixture was plated onto LB agar plates. Plaques were blotted onto nitrocellulose membranes. Membranes were rinsed in Tris-buffered saline with 0.01% Tween-20 (TBST) 3 times and subsequently in blocking solution (20% (v/v) fetal serum in TBST). After washing the membranes in TBST, the first antibody (rabbit anti equistatin IgG) in TBST was added and membranes were treated in solution overnight at 4° C. Afterthat, membranes were washed three times with TBST, and treated with second antibody (goat anti rabbit IgG.—horse raddish peroxidase). After final washing in TBST, a visualization with diaminobenzidine as a substrate was performed. Three positive clones were isolated from agar plates and after re-plating, phages were eluted from the surface of the agar plates with TE buffer (5 ml per plate). Phage DNA was isolated using Wizard Lambda Preps DNA isolation kit (Promega) according to the manufacturer's procedure. After restriction analysis with 2 μl of EcoRI restriction enzyme (10U/μl) per 3 μg of λDNA and size fractionation on 1% agarose gel, cDNA inserts were excised, purified with glass milk and subcloned into EcoRI cloning site of pUC19 plasmid. Whole ligation mixture (10 μl of each sample) was transformed into DH5α *E. coli* cells by incubating the 100 μl of highly competent cells (O.D.$_{550}$=0.6) and 10 μl of ligation mixture in a water bath (42° C.) for 45 seconds. After addition of LB medium (900 μl) and 1 h incubation (37° C., 250 rpm), bacterial mixture was plated onto LBA plates, supplemented with X-gal and IPTG and after overnight incubation (37° C.), white colonies were transferred into 5 ml of LB medium and incubated for an additional 16 hours (37° C., 250 rpm). Plasmids were isolated using Wizard Plasmid Purification System (Promega) according to manufacturer's instructions and analysed by nucleotide sequencing using T7 DNA polymerase (T7 sequencing kit, Parmacia) and [$^{35}$S]dATP S Amersham). Sequencing of selected cDNA clones resulted in the full length cDNA clone given in FIG. 1. The DNA sequence of FIG. 1 corresponds to SEQ ID NO:1. The protein dequence of FIG. 1 corresponds to SEQ ID NO:2.

Example 3
Expression of Recombinant Equistatin cDNA in *Escherichia coli*

Two primers were used to amplify the mature protein of equistatin and to clone it as an NcoI-NotI fragment behind the g3 signal peptide present in the *E. coli* expression vector pB3. Primer is was PDEI-1: CGC GCC ATG GCG AGT CTA ACC AAA TGC CAA (SEQ ID NO:9) and primer 2 was PDEI-2: GGG TGC GGC CGC GCA TGT GGG GCG TTT AAA (SEQ ID NO: 10). Correct inserts were sequenced to check for sequence errors and one clone was selected for obtaining recombinant protein.

Recombinant equistatin was obtained by growing a single colony of *E. coli* strain HB2151 with the plasmid pB3, carrying the equistatin cDNA, overnight in 5 ml of LB growth medium with ampicillin (100 mg/l, rinal conc.) at 37° C., 250 rpm. 5 ml of the overnight culture was used for the inoculation of 800 ml of LB medium with ampicillin (100 mg/l, final conc.) in a 2 l flask. Cells are grown with shaking (30° C. at 250 rpm) to O.D.600=0.5. After that, an IPTG stock solution is add to a final conc. of 1 mM and growth of cells is continued using the same conditions as above for an additional 6h. Cells are placed on ice for 1 h, then pelleted at 4000Xg for 10 min at 4° C. and resuspended in 50 ml of ice cold 10 mM MgSO4. Suspension is olaced at −20° C. untill the liquid is completely frozed and afterthat, content is thawed by submerged the flask with the sample into a water bath (30° C.). Immediatelly afrer re-thawing, cells are removed by centrifugation at 6000Xg for 10 min at 4° C. and supernatant is stored at −20° C. for subsequent affinity purification on papain-sepharose.

Example 4
Purification and Characterization of Recombinant Equistatin
A. Affinity Purification Using Papain-Sepharose:

10 ml of a papain-sepharose slurry is mixed with a 15 ml of 0.02 M NaOH for 10 min. Subsequently, the slurry is applied on a 15 ml column with glass fritte. The column was washed 3× with 30 ml of 100 mM Tris buffer, pH 7.0 and finally, with 10 ml of 50 mM MES buffer, pH=6.5 (with the addition of cysteine to a final conc. 0.6 mg/ml). Supernatant from 1 l of bacterial culture, obtained as described above (example 3) is dropwise applied on a column. Papain-sepharose is then washed with 20 ml of 50 mM MES buffer, pH=6.5 (without cysteine) and with 50 ml of 20 mM Tris buffer, pH=7.5. Sample is recovered by eluting the column with the 20 ml of 20 mM Tris buffer, pH=10.3 (without adjusting the pH with HCl), 20% DMSO. Purified equistatin was dialyzed against $H_2O$ and concentrated using Sartricon mini-concentrators in order to achieve a final concentration of 350 µM.

B. Stoichiometry and Inhibition Constants for Recombinant Equistatin

In a microtiterplate 20 µl papain solution (a fresh solution of 1 mg/ml (Sigma) in MES buffer titrated with E-64 to determine the active fraction, usually 17%) is combined with 0–80 µl of known protein concentration. MES buffer (50 mM MES, pH 6.5; 0.6 mg/ml L-cysteine; 1 mg/ml BSA fraction V) is added to a final volume of 150 µl. The mixture is incubated for 30 min at room temperature and subsequently 50 µl of substrate solution (60 µl of 15 mg/ml Z-Phe-Arg-pNA dissolved in methanol is diluted in in 940 µl MES buffer before use). The plate is immediately placed in the nicrotiterplate reader and measured at 405 nm. Readings up to an OD600 of 0.3 are linear. Rates of change are used to determine the activity with increasing amounts of inhibitor. Results are graphically represented and at stoichiometric concentrations the amount of dissociated complex is determined to determine the apparent equilibrium dissociation constant (Ki). These results established that one molecule of equistatin will inhibit approximately 1 molecule of papain. The apparent equilibrium dissociation constant for papain was estimated to be 0.6 nM in agreement with the data published for the purified protein (Lenarcic et al. (1997) J. Biol. Chem. 272: 13899–13903.

Figure 3:
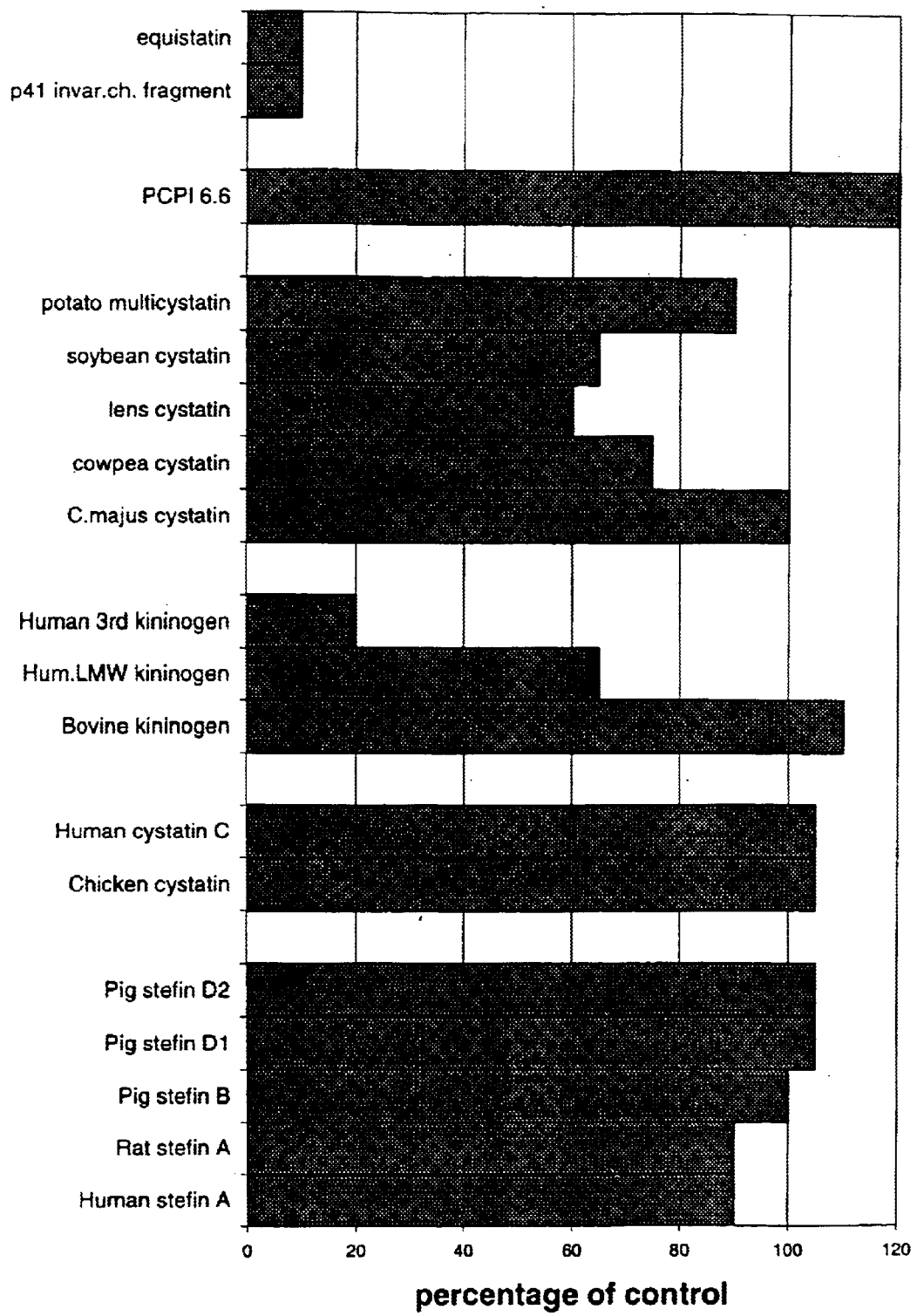
FIG. 3 shows the in vitro effects of a wide range of different cysteine protease inhibitors on cysteine proteases of Colorado potato beetle larvae (*Leptinotarsa decemlineata*) that are insensitive to the endogenous cysteine protease inhibitors of the host plant potato.
Figure 4A:
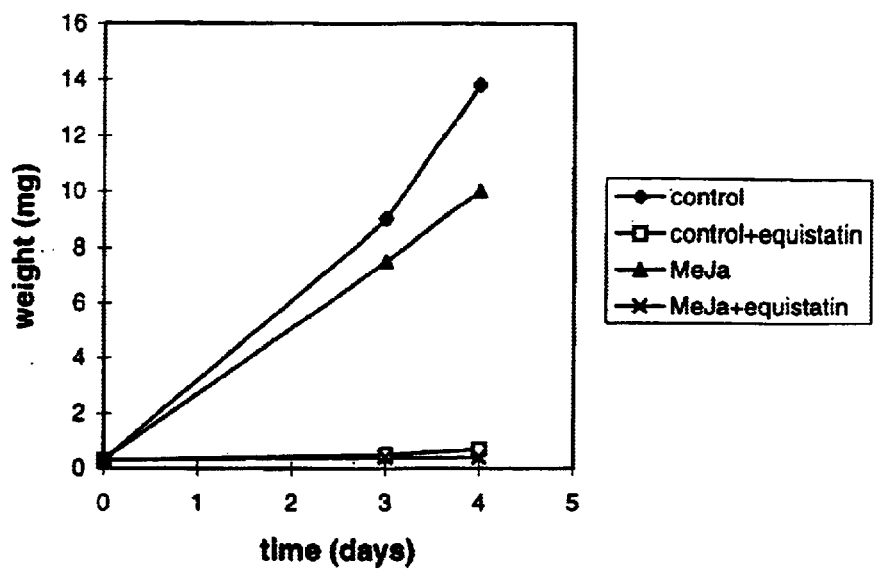
FIG. 4 shows the effects of equistatin on growth and mortality of Colorado potato beetle larvae
Figure 4B:
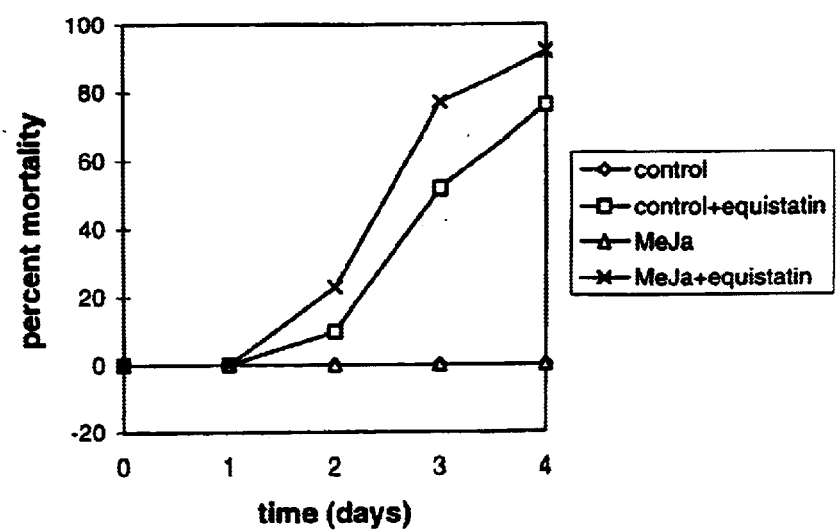

Example 5
In Vitro Inhibition of Colorado Potato Beetle Midgut Protease Activity Guts of final instar Colorado potato beetle larvae reared on methyl jasmonate induced plants were isolated and extracted essentially as described (Bolter and Jongsma, *J. Insect Physiol.* 41: 1071–1078). In these gut extracts the proteases that are sensitive to the protease inhibitors of potato are already complexed. The residual protease activity is composed of potato protease-inhibitor-insensitive proteases which were induced in response to the methyl jasmonate induced potato inhibitors. These proteases are the proteases that render the beetle larvae insensitive to protease inhibitor defense of the potato plant. Wle tested a broad range of different cysteisie protease inhibitors for activity specifically against these induced potato protease inhibitor-insensitive cysteine protesses. Nearly all of these inhibitors were purified at the Jozef Stefan Institute in Slovenia. Testing their potential against Colorado potato beetle was done using both general protein substrates (azocasein, table 2) as well as specific synthetic substrates (L-Arg-pNA, table 3; pGlu-Phe-Leu-pNA, table 4; Z-Phe-Arg-pNA, table 5; Z-Arg-Arg-pNA, table 6). In specific cases inhibitors were tested at two concentrations, eauimolar and in excess to the protease, in order to obtain an indication of the tightness of the complex. Most of the tested inhibitors were either inactive or only weakly inhibitory. Only the type I repeated thyroglobulin domain cysteine protease inhibitors that were tested (purified p41 invariant chain fragment and purified equistatin) were consistently highly active against the endo- and exoproteolytic activity of colorado potato beetle larvae assayed (tables 2–6; FIG. 4). Importantly, this class of inhibitors was capable of inhibiting nearly all general cysteine protease activity. The equistatin peptide molecule and a functional derivative thereof were not very active against the aminopeptidase-like cysteine protease activity. Recombinant human stefin A was highly active against this type of activity. The best combination of inhibitors for full toxicity against the Colorado potato beetle would therefore be a combination of equistatin or p41 invariant chain fragment and stefin-like inhibitors.

TABLE 3

Effect of different cysteine protease inhibitors on general proteolytic activity of Colorado potato beetle larval gut extracts as measured with azocasein

| Family of cysteine protease inhibitor | name | Residual activity in excess of inhibitor |
|---|---|---|
| Type I cystatins | human stefin A | 90% |
| | rat stefin A | 90% |
| | porcine stefin B | 100% |
| | porcine stefin D1 | 105% |
| | porcine stefin D2 | 105% |
| Type II cystatins | chicken cystatin | 105% |
| | human cystatin c | 105% |
| Type III cystatins | bovine kininogen | 110% |
| | human LMW kininogen | 65% |
| | hum kininocen 3rd domain | 20% |
| Phytocystatins | *Chelidonium majus* cystatin | 100% |
| | cowpea cystatin | 75% |
| | lens cystatin | 60% |
| | soybean cystatin | 65% |
| | potato multicystatin | 90% |
| | bromelain inhibitor | 110% |
| Type I domain of | p41 invariant chain | 10% |

TABLE 3-continued

Effect of different cysteine protease inhibitors
on general proteolytic activity of Colorado potato
beetle larval gut extracts as measured with azocasein

| Family of cysteine protease inhibitor | name | Residual activity in excess of inhibitor |
|---|---|---|
| thyroglobulin | fragment equistatin | 10% |
| Plant Kunitz CPI | PCPI 6.6 | 120% |

TABLE 4

Effect of different cysteine protease
inhibitors on amino-peptidase activity
as measured with L-Arg-pNA

| | % of residual activity | |
|---|---|---|
| | excess inhibitor | equimolar |
| equistatin and p41 invariant chain fragment | 75% | 85% |
| human stefin A | 10% | 60% |
| kininogens | 75% | n.d. |
| phytocystatins from *Fabaceae* | 75% | n.d. |

TABLE 5

Effect of different cysteine protease
inhibitors on specific tri-peptidil-peptidase and
endoprotease activity as measured with pGlu-Phe-Leu-pNA

| | % of residual activity | |
|---|---|---|
| | excess inhibitor | equimolar |
| equistatin and p41 invariant chain fragment | −5% | 10% |
| human stefin A | 90% | 95% |
| kininogens | 20% | n.d. |
| phytocystatins from *Fabaceae* | 70% | n.d. |

TABLE 6

Effect of different cysteine protease inhibitors on board
spectrum endoprotease activity as measured with Z-Phe-Arg-pNA.

| | % of residual activity | |
|---|---|---|
| | excess inhibitor | equimolar |
| equistatin and p41 invariant chain fragment | 20% | 30% |
| human stefin A | 80% | 95% |
| kininogens | −20% | n.d. |
| phytocystatins from *Fabaceae* | 50% | 65% |

TABLE 7

Effect of different cysteine protease inhibitors on narrow
spectrum endoprotease activity as measured with Z-Arg-Arg-pNA

| | % of residual activity | |
|---|---|---|
| | excess inhibitor | equimolar |
| equistatin and p41 invariant chain fragment | −5% | 20% |

TABLE 7-continued

Effect of different cysteine protease inhibitors on narrow
spectrum endoprotease activity as measured with Z-Arg-Arg-pNA

| | % of residual activity | |
|---|---|---|
| | excess inhibitor | equimolar |
| human stefin A | 90% | n.d. |
| kininogens | 10% | n.d. |

Example 6

In Vitro Inhibition of Protease Activity of Adult Western Flower Thrips, and Leafminer Flies, and Final Instar Larvae of Colorado Potato Beetle and Western Corn Rootworm as Measured with FITC-Labeled Hemglobin.

Adult western flower thrips (*Frankliniella occidentalis*) and leafmirer flies (*Liriomyza trifolii*) adult were harvested from a culture maintained on chrysanthemum plants and complete thrips and flies were homogenized in extraction on buffer (200 mM β-alanine-HCl, pH 3.5) in a volume of 5 times the weight of the insects. The buffer pH was at the previously determined pH optimum of protease activity towards hemoglobin. Final instar Colorado potato beetle larvae maintained on potato plants as described in example 5 were checked for gut aspartic protease activity by preparing a total gut extract in pH 3 buffer which is optimal for Colorado potato beetle aspartic proteases (200 mM glycine, pH 3). Guts were homogenized in 100 µl buffer per gut. Third instar western corn rootworm larvae maintained on corn roots were used to remove the guts. Ten guts were homogenized in 100 µl water and spinned twice to remove insoluble material. Two types of buffers were used in the enzymatic assay. One with a pH presumably favoring cysteine proteases (50 mM MES, pH 6.5; 0.6 mg/ml L-cysteine) and one for detecting aspartic proteases (200 mM glycine, pH 3). Supernatants were stored at −20° C.

2 µl gut extract was combined with 2 µl inhibitor (2 mM pepstatin in methanol, 4 mM E64 in water, 2 mg/ml recombinant equistatin in water. The concentration of the other proteinaceous inhibitors was not known exactly). Appropriate buffers were added to a final volume of 100 µl. After 15' preincubation 20 µl substrate (5 mg/ml FITC-hemoglobin) was added and incubated for 30–45 min at 37 C.

Reaction was stopped by the addition of 100 µl 10% TCA. Tubes were centrifuged and 100 µl supernatant mixed with 100 µl 10 N NaOH was measured on a fluorimeter for the extent of hemoglobin hydrolysis. Measurements were done in duplicate on one (thrips, leafminer and western corn rootworm), or three (Colorado potato beetle) different gut extracts and varied by a maximum of +/−5%.

The effects of different cysteine and aspartate protease inhibitors are listed in table 9. They provide the effects of different protease inhibitors (PIs) against "PI-insensitive proteases" of thrips adults, and leafminer flies on chrysanthemum, of Colorado potato beetle on potato and corn rootworm on corn because induced PIs present in the plantmaterial and ingested by the insect will be present in the extract in complex with the susceptible proteases.

*Thrips protease activity can be* 92% inhibited by E-64 (cysteine PI) and 16% by pepstatin (aspartic PI) at pH 3.5 which is optimal for thrips general protease activity. Apparently, aspartic proteases are not not dominant in this insect. P41-invariant chain resulted in 87% inhibition whereas equistatin afforded 95% inhibition of protease activity. Clearly both P41-invariant chain (cysteine PI) and equistatin (cysteine/aspartic PI) are both good inhibitors of thrips cysteine proteases, though equistatin may be slightly better due to the additional inhibition of aspartic proteases.

Leafminer proteases can only be fully inhibited by a combination of E64 (cysteine PI) and pepstatin (aspartic PI) (97%). Potato cystatin and Kunitz PCPI8.3 are both cysteine protease inhibitors which are capable of inhibiting 63% comparable to 73% by E64. Addition of equistatin to those two inhibitors results in 92% inhibition, demonstrating that equistatin must have leafminer aspartic protease inhibitor activity apart from cysteine protease inhibitor activity. For optimal control of leafminer a combined use of equistatin with potato cystatin and Kunitz PCPI8.3 may be necessary.

Colorado potato beetle proteases at pH3 can only be fully inhibited (97%) by a combination of E64 (24%) and pepstatin (82%). Addition of equistatin to either E64 or pepstatin increases the inhibition by 42% (24%+42%=66%) and 12% (82%+12%=94%) respectively demonstrating that equistatin inhibits more than 50% of both aspartic and cysteine protease activity at this pH. equistatin alone inhibits 62% of total protease activity at this pH. Apparently, the partial inhibition at pH 3 combined with nearly full inhibition at pH 6.5 (example 5) is sufficient for full control of this insect (example 7).

Western corn rootworm is known to possess a complement of both cysteine and aspartic proteases (Gillikin et al.(1992) *Arch. Insect Biochem. Physiol.* 19: 285–298). The effects of equistatin, E64 and pepstatin were tested at two different pH values. The data in table 9 show that equistatin almost completely inhibited all cysteine and aspartic protease activity (93% at pH 6.5 and 98% at pH 3) and was even more powerful than the combination of E64 and pepstatin (79% and 89% resp.). These in vitro results are even better than the in vitro results for Colorado potato beetle in examples 5 and 6 and indicate that equistatin can be expected to be toxic towards western corn rootworm when expressed in corn roots.

TABLE 8

In vitro inhibition assays measuring residual protease activity in extracts of different insects.

| inhibitors | thrips pH 3.5 | leaf-miner pH 3.5 | colorado potato beetle pH 3 | western corn rootworm pH 6.5 | western corn rootworm pH 3 |
|---|---|---|---|---|---|
| control | 100% | 100% | 100% | 100% | 100% |
| E64 | 8% | 27% | 76% | 51% | 35% |
| E64/equistatin (EI) | n.d. | n.d. | 34% | 29% | 8% |
| Pepstatin | 84% | 46% | 18% | 58% | 45% |
| Pepstatin/EI | n.d. | n.d. | 6% | 6% | 0% |
| E64/Pepstatin | n.d. | 3% | 3% | 21% | 11% |
| EI | 5% | 24% | 36% | 7% | 2% |
| p41 invariant chain | 13% | 43% | n.d. | n.d. | n.d. |
| p.cystatin | n.d. | 73% | n.d. | n.d. | n.d. |
| PCPI8.3 | n.d. | 43% | n.d. | n.d. | n.d. |
| API | n.d. | 37% | n.d. | n.d. | n.d. |
| p.cystatin/PCPI8.3 | n.d. | 8% | n.d. | n.d. | n.d. |
| p.cystatin/PCPI8.3/API | n.d. | 7% | n.d. | n.d. | n.d. |
| p.cystatin/PCPI8.3/EI | n.d. | n.d. | n.d. | n.d. | n.d. |
| bean cystatin | 14% | n.d. | n.d. | n.d. | n.d. |

Recombinant Kunitz PCPI8.3 (Stiekema et al. (1987) *Plant Molec. Biol.* 11: 255–269) was produced in the yeast *Pichia pastoris* and purified from culture supernatant by cation exchange chromatography.

Recombinant potato cystatin (p.cystatin) represents a monomer of multicystatinr cloned by RT-PCR from potato cv. Superior and expressed and ourified as a fusion protein with glutathione-S-transferase (Pharmacia).

Equistatin was either purified from sea anemone (Lenarcic et al.(1997) *J. Biol. Chem.* 272: 13899; Lenarcic et al. *J. Biol. Chem.* 273: 12682) (thrips and leaforminer assays) or recombinant from *E. coli* (Colorado potato beetle and Western corn rootworm assays)

Aspartic protease inhibitor (API) was purified from potato (Kreft et al. (1997) *Phytochemistry* 44: 1001–1006)

Example 7

Toxicity of Equistatin Towards Colorado Potato Beetle Larvae

Potato tubers of cultivar Surprise (*Solanum tuberosum*) were sprouted. Sprouted tubers were planted in 1 l pots and grown for 3–4 weeks at a 22/18° C., 16/8 hr day night rhythm. Plants 10–15 cm high were placed in glass jars together with a paper wick on which 2 ul methyl jasmonate was pipeted. Jars were sealed immediately with parafilm and placed in a climate chamber of 30° C. with continuous light. Control plants were placed in a chamber of 25° C. with a 16–8 hr day night rhythm. After one day at 30° C. plants were taken from the jars and placed in the same chamber as the control. Plants were used on day 3. Freshly treated plants were used for each subsequent day of feeding. This treatment resulted in high endogenous PI levels in the methyljasmonate treated plants. The top meristems were removed from the plants and painted on both sides with a 175 $\mu$M solution of recombinant equistatin in 0.3% agar obtained by mixing 1:1 a stock solution of 350 $\mu$M equistatin with 0.6% water agar. Controls were painted with 0.3% water agar. The agar solution was applied at a concentration of 30 $\mu$l/cm2.

The final concentration on the leaf was estimated to be 70 $\mu$M which is equivalent to 1.4 mg/g leaf. Painted leaves were placed in a tube containing 0.4% agar and out on top of a filterpaper inside a petridish. 21–26 newly hatched Colorado potato beetle larvae were placed on the leaves and the petridish was put in an incubator set at 28° C. Everyday fresh painted leaves replaced the old ones.

In tables 9 and 10 the effects on growth and mortality of the Colorado potato beetle larvae are summarized. It is apparent from these tables that equistatin applied on control plants with low levels of endogenous protease inhibitors is capable of severely reducing development and causing high mortality rates on the larvae already after 4 days. Applying equistatin on leaves containing high endogenous PI levels induced by prior treatment with methyl jasmonate further enhances the toxic effects of this inhibitor, however. This confirms the expected synergistic effect of this inhibitor because it specifically targets the "PI-insensitive proteases" of Colorado potato beetle larvae.

TABLE 9

Effect of recombinant equistatin on growth of Colorado potato beetle larvae

| treatment | day 1 | day 2 | day 3 | day 4 |
|---|---|---|---|---|
| control | n.d. | n.d. | 9 | 13.8 |
| control + equistatin | n.d. | n.d. | 0.5 | 0.7 |
| MeJa-control | n.d. | n.d. | 7.5 | 10 |
| MeJa control + equistatin | n.d. | n.d. | n.g. | n.g. |

21–26 larvae per experiment were assayed
Larval weights are given in mg/larvae;
n.d. is not determined;
n.g. is not grown or dead

TABLE 10

Effect of recombinant equistatin on percent mortality of Colorado potato beetle larvae

| treatment | day 1 | day 2 | day 3 | day 4 |
|---|---|---|---|---|
| control | 0 | 0 | 0 | 0 |
| control + equistatin | 0 | 10 | 52 | 76 |
| MeJa-control | 0 | 0 | 0 | 0 |
| MeJa control + equistatin | 0 | 23 | 77 | 92 |

21–26 larvae per experiment were assayed

Example 8
In Vivo Effect of Equistatin on Oviposition Rate of Thrips

A sample of 142 μM recombinant equistatin purified as described in example 4 was assayed for activity towards thrips. Sample was acidified with HCl to pH 3 to stabilize the equistatin protein. Controls contained acidified water or 2.5 mg/ml BSA dissolved in acidified water. The oviposition rate of thrips females was assayed using so-called Murai cages. Briefly, perspex tubes closed on side with a fine gauze were inoculated with 10 females and bee pollen. Tubes were closed with parafilm and 300 μl fluid was placed on top of the parafilm. A second layer of parafilm enclosed the fluid. Pollen and sample fluid were replaced every day for two days. Eggs deposited in the liquid sample were counted on day 2.

TABLE 11

Oviposition rate of adult females two days after being placed on different diets

| diet | eggs per female per day | relative percentage |
|---|---|---|
| BSA | 1.8 | 100% |
| water | 1.5 | 83% |
| equistatin | 0.3 | 17% |

Example 9
Modification of the Equistatin Gene for Improved Expression in Plants The equistatin cDNA contains in the coding region several potential plant polyadenylation signals, mRNA instability motifs and a suboptimal codon usage for expression in plants. To improve the level of gene expression in plants these motifs may be removed and codons may be optimized by site specific mutagenesis without altering the primary protein sequence. Below an example of the modifications required to obtain improved gene expression in potato are given. The top strand represents the coding part of the cDNA clone, below that the suggested modifications of the cDNA sequence are given and below that the protein coding sequence is given using the one-letter code for the amino acid residues. The DNA sequence below corresponds to SEQ ID. NO: 3. The protein sequence corresponds to SEQ ID NO: 4.

```
   1 ATGGCTCTTAGCCAAAACCAAGCCAAGTTTTCCAAAGGATTCGTCGTGATGATTTGG
                   G     G              G
 -32 M  A  L  S  Q  N  Q  A  K  F  S  K  G  F  V  V  M  I  W

60 GTACTATTCATTGCTTGTGCTATAACTTCAACTGAAGCTAGTCTAACCAAATGCCAACAG
                            C                       G
 -13 V  L  F  I  A  C  A  I  T  S  T  E  A  S  L  T  K  C  Q  Q
                                         -1  +3

120 CTCCAGGCCTCGGCTAACAGTGGTCTGATAGGTACTTATGTACCACAATGCAAAGAAACG
       G     T  T                                               T
   8 L  Q  A  S  A  N  S  G  L  I  G  T  Y  V  P  Q  C  K  E  T

180 GGAGAGTTCGAAGAAAAACAATGCTGGGGATCGACTGGTTACTGTTGGTGTGTGGATGAA
             T        G              T
  28 G  E  F  E  E  K  Q  C  W  G  S  T  G  Y  C  W  C  V  D  E

240 GATGGAAAAGAGATTCTAGGAACCAAGATCCGTGGATCTCCGGATTGCAGCCGCAGAAAA
                         T  A                 A  C     T
  48 D  G  K  E  I  L  G  T  K  I  R  G  S  P  D  C  S  R  R  K

300 GCCGCGTTAACACTTTGCCAGATGATGCAAGCCATCATTGTTAATGTCCCTGGTTGGTGT
       T  C                                   G
  68 A  A  L  T  L  C  Q  M  M  Q  A  I  I  V  N  V  P  G  W  C

360 GGCCCTCCATCGTGTAAAGCTGACGGCAGTTTTGACGAGGTTCAGTGCTGCGCAAGTAAT
       A        A
  88 G  P  P  S  C  K  A  D  G  S  F  D  E  V  Q  C  C  A  S  N

420 GGAGAATGCTACTGTGTGGATAAGAAAGGAAAAGAACTTGAAGGCACAAGACAACAGGGA

108 G  E  C  Y  C  V  D  K  K  G  K  E  L  E  G  T  R  Q  Q  G

480 AGGCCAACCTGCGAAAGACACCTAAGCGAATGCGAGGAAGCTCGAATCAAGGCGCATTCA
                                           G     T        A
 128 R  P  T  C  E  R  H  L  S  E  C  E  S  A  R  I  K  A  H  S

540 AACAGTCTTCGTGTTGAGATGTTCGTGCCAGAGTGTTTAGAAGATGGATCATATAACCCA
                                                       T  C     T
 148 N  S  L  R  V  E  M  F  V  P  E  C  L  E  D  G  S  Y  N  P

600 GTACAGTGCTGGCCTAGCACAGGATACTGTTGGTGCGTCGATGAAGGAGGGGTAAAGGTA
                                                                T
```

-continued

```
168 V Q C W P S T G Y C W C V D E G G V K V

660 CCAGGTTCCGATGTCAGATTTAAACGCCCCACATGCTAA
              C        C    T
188 P  G  S  D  V  R  F  K  R  P  T  C ---
                                        199
```

Example 10
Construction of Plant Vectors for Expression of Equistatin.

The potato Cab promoter (Nap et al. (1993) *Plant Mol. Biol.* 23: 605–612) was amplified from plasmid pPPG by PCR using the primers P1-POTCAB and P2-POTCAB. Similarly the Nos terminator was amplified from plasmid pPPG using the primers NOS-TERM-DN and NOS-TERM-UP. The promoter and terminator fragment were cut with the restriction enzymes &2EcORI and SacI and ligated into an EcoRI digested pUCAP vector (Van Engelen et al. (1995) *Transgenic Research* 4: 288–290). A correct clone was selected and sequenced. This clone, pUCCAB1 was digested with NcoI and BglII and used to subclone the equistatin coding region which was amplified by PCR from plasmid pB3-equistatin using the primers EQUISTAT-DN and EQUISTAT-BGL and also cut with NcoI and 3glII. A correct clone was selected and the insert equistatin cDNA clone was sequenced. A correct clone, pUCCAB1-equistatin, was digested with EcoRI. The EcoRI fragment containing the equistatin expression cassette was ligated into the plant vector pBINPLUS (Van Engelen et al. (1995) *Transaenic Research* 4: 288–290) which was also digested with EcoRI. A correct clone was selected. This clone, pCAB1-equistatin, was electroporated to electrocompetent *Agrobacterium tumefaciens* AGL-0 cells. Positive clones were selected on LB-medium containing 100 mg/l kanamycin.

TABLE 12

PCR-primers used for PCR-amplication

| name | DNA |
|---|---|
| P1-POTCAB: | 5'-GGGGGGGAATTCCTGACCTCTTACTAACTCG |
| P2-POTCAB: | 5'-GGGGGGGAGCTCAGATCTTGCATGG-TTTTTCTTCTCTTTTTTTTG |
| NOS-TERM-DN: | 5'-AGATCTGAGCTCTCGTTCAAACATTTCGCA |
| NOS-TERM-UP: | 5'-AAGCTTGAATTCGATCTAGTAACATAG |
| EQUISTAT-DN: | 5'-GGGGCCATGGCTCTTAGCCAAAAC |
| EQUISTAT-BGL: | 5'-GGGGGAGATCTTTAGCATGTGGGGCGTTTAAA |

Example 11
Transformation of Potato with Plant Vectors Containing the Equistatin cDNA On day 1 an *Agrobacteriunm tumefaciens* culture of AGL0 containing the pCAB1-equistatin binary vector was started in 50 ml LB-medium containing 50 mg/l kanamycin and shaken for 2 days at 28° C. On day 2 internodes from an in vitro culture of the potato cultivar Desiree line V were cut into 0.5–1 cm pieces and placed on R3B medium (30 g/l sucrose, 4.7 g/l Murashige and Skoog salts, pH 5.8 (KOH), 8 g/l purified agar, 2 mg/l NAA and 1 mg/l BAP) which was covered with 2 sterile filterpapers that had previously been soaked in 2 ml PACM medium (30 g/l sucrose, 4.7 g/l Murashige and Skoog salts, 2 g/l casein hydrolysate, pH 6.5 (KOH) 1 mg/l 2,4-D and 0.5 mg/l kinetine). The dishes were taped with parafilm and incubated overnight at 24° C. under a regime of 16 h light. At day 3 the *A. tumefaciens* culture was poured in a sterile petridish containing the explants. After 5–10 min explants are removed from the culture, placed on a sterile filter paper to remove excess *Agrobacteria* and placed back on the R3B medium containing dishes after first removing the top filter paper (leaving one behind). Dishes with explants were further incubated at 24° C. and 16 h light until day 5, when the explants were transferred to dishes containing ZCVK medium (20 g/l sucrose, 4.7 g/l Murashige and Skoog salts, pH 5.8 (KOH), 8 g/l purified agar, 1 mg/l zeatine, 200 mg/l vancomycin, 100 mg/l kanamycin, 200 mg/l claforan). On day 19 and subsequently every 3–4 weeks explants were transferred to new ZCVK medium. When shoots appeared shoots were transferred to Murashige and Skoog medium containing 20% sucrose (MS20). After rooting plants were transferred to the green house.

Example 12
Bioassays of Colorado Potato Beetle Larvae on Transgenic Potato Plants Expressing Equistatin The equistatin cDNA sequence optimized for expression in potato plants was cloned into the pCAB1 vector and transformed to line V. Eight different primary transformants were tested for resistance to newly hatched Colorado potato beetle larvae. Leaves were removed fromit young plants in the greenhouse and inserted into a tube containing 0.4% purified water agar and placed in a petridish with filter paper. Six randomly picked newly hatched larvae were inoculated per leaf. Leaves were replaced after two days with fresh leaves. On day 3 larval weights were measured for each larva individually. Table 13 provides the results, indicating that 3 out of 6 transformants significantly retarded growth of the larvae. Some plants lack resistance most likely due to low expression caused by a suboptimal position of the T-DNA insertion in the plant genome. Plants were too young to extend the experiment for longer out of lack of leaf material, but it was observed that the larvae on pCAB-EIM-1 were all dead on day 4. The presence of the equistatin protein was confirmed by western blotting and estimated to be >0.1% in transgenics which showed resistance.

TABLE 13

Results of bioassay on transgenic potato plants transformed with the equistatin gene optimized for expression in plants.

| Plant[a] | Larval weight[b] |
|---|---|
| Line V | 9.93 a |
| pBINPLUS | 10.67 a |
| pCAB1-EIM-1 | 4.03 b |
| pCAB1-EIM-2 | 5.45 b |
| pCAB1-EIM-3 | 8.77 a |
| pCAB1-EIM-6 | 8.92 a |
| pCAB1-EIM-7 | 8.55 a |
| pCAB1-EIM-8 | 5.85 b |

TABLE 13-continued

Results of bioassay on transgenic potato plants transformed with the equistatin gene optimized for expression in plants.

| Plant[a] | Larval weight[b] |
|---|---|
| PCAB1-EIM-9 | 9.18 a |
| pCAB1-EIM-10 | 11.15 a |

[a]Plants tested were Line V, an in vitro plant transferred to the greenhouse simultaneously with the transformants; pBINPLUS, a line V transformant with the empty vector without the promoter-gene cassette; pCAB1–10, the first 8 line V transformants with the optimized equistatin gene under the control of the CAB promoter.
[b]Average larval weighs (mg) of six larvae. The letter code following the weights of the larvae indicates significance as determined by ANOVA.

Example 13

Isolation of Homologous Gene Sequences From Other Organisms in Order to Find or Generate Improved Inhibitors.

The 6 amino acid residues Gly-Tyr-Cys-Trp-Cys-Val (SEQ ID NO:17) which are strongly conserved among type I repeated thyroglobulin cysteine and aspartic protease inhibitors, whether from human, salmon or sea anemone sources, may be used to isolate homologous sequences with improved specificities. Degenerate PCR primers may be designed based on these sequences to amplify genomic or cDNA fragments which can be used as probes to isolate the entire coding sequence from for example cDNA libraries or by 5'RACE experiments from purified mRNA. Any organism including insects and plants may be used as new sources of type I repeated thyroglobulin domains. Collections of genes may be used in gene shuffling experiments to isolate new specificities.

---

What is claimed is:

1. A method of protecting a plant or a part of said plant against insect or nematode infestation by one or more insects or nematodes having digestive cysteine proteases, wherein the method comprises the steps of:
   (a) culturing cells or tissue from the plant;
   (b) inserting into the genome of the cells or tissue a DNA construct comprising a nucleic acid encoding the cysteine protease inhibitor of SEQ ID NO:2 operably linked to a promoter sequence active in the plant, wherein the inhibitor is expressed at levels which provide an insect- or nematode-controlling amount of said inhibitor; and
   (c) regenerating a resistant whole plant from the cells or tissue.

2. The method according to claim 1, which comprises the further step of (d) sexually or clonally reproducing the whole plant to produce a reproduced plant, wherein the reproduced plant has at least one copy of the DNA construct present in its cells.

3. The method according to claim 2, further comprising the steps of:
   (d) sexually crossing the reproduced plant with an insect or nematode susceptible plant;
   (e) recovering seeds from the cross;
   (f) growing progeny plants from the seeds; and
   (g) selecting insect or nematode resistant plants from the progeny plants.

4. The method according to claim 3, which comprises the further steps of repetitively;
   (h) backcrossing the resistant plants with substantially homozygous plants from an insect or nematode susceptible variety; and
   (i) selecting for expression of both insect or nematode resistance and characteristics of the susceptible variety among the progeny of the backcross, until the desired percentage of the characteristics of the susceptible variety are present in the progeny along with the insect or nematode resistance.

5. The method of claim 1, wherein the nucleic acid is SEQ ID NO:1.

6. The method of claim 1, wherein the nucleic acid is SEQ ID NO:3.

7. A transgenic plant that is resistant to attack by one or more insects or nematodes having digestive cysteine proteases, wherein said transgenic plant comprises a nucleic acid encoding a protein of SEQ ID NO:2 and wherein the plant expresses an insect- or nematode-controlling amount of the protein.

8. The plant of claim 7, wherein the nucleic acid is SEQ ID NO:1.

9. The plant of claim 7, wherein the nucleic acid is SEQ ID NO:3.

10. An expression vehicle comprising a promoter effective to promote expression of a downstream coding sequence in plant cells, operatively linked to a nucleic acid encoding a protein of SEQ ID NO:2, and a termination sequence effective to terminate transcription or translation of the protein product in plant cells, wherein the expression vehicle expresses in plant cells insect-controlling amounts of the protein.

11. The expression vehicle of claim 10, wherein the nucleic acid is SEQ ID NO:1.

12. The expression vehicle of claim 10, wherein the nucleic acid is SEQ ID NO:3.

13. A host cell transformed with the expression vehicle of claim 10.

* * * * *